United States Patent
McKay

(10) Patent No.: US 9,307,971 B2
(45) Date of Patent: Apr. 12, 2016

(54) SURGICAL RETRACTOR INSTRUMENT SYSTEMS AND METHODS OF USING THE SAME

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 874 days.

(21) Appl. No.: 12/697,403

(22) Filed: Feb. 1, 2010

(65) Prior Publication Data

US 2011/0190588 A1    Aug. 4, 2011

(51) Int. Cl.
| A61B 1/32 | (2006.01) |
| A61B 17/02 | (2006.01) |
| A61B 17/00 | (2006.01) |
| A61B 19/00 | (2006.01) |

(52) U.S. Cl.
CPC ... *A61B 17/0206* (2013.01); *A61B 2017/00017* (2013.01); *A61B 2017/00115* (2013.01); *A61B 2017/00128* (2013.01); *A61B 2017/00398* (2013.01); *A61B 2017/00539* (2013.01); *A61B 2017/00544* (2013.01); *A61B 2017/0212* (2013.01); *A61B 2019/464* (2013.01); *A61B 2019/465* (2013.01)

(58) Field of Classification Search
CPC ...... A61B 1/32; A61B 17/02; A61B 17/0206; A61B 17/0218; A61B 17/025; A61B 17/3423; A61B 2017/00039; A61B 2017/0256; A61B 17/0256; A61B 17/0293; A61B 1/313; A61B 1/3132; A61B 1/3135; A61B 1/317
USPC .................................. 600/201–246
See application file for complete search history.

(56) References Cited

U.S. PATENT DOCUMENTS

| 1,706,500 | A | * | 3/1929 | Smith | A61B 17/02 600/232 |
| 4,049,952 | A | * | 9/1977 | Forsslund | G04F 1/005 377/16 |
| 4,215,581 | A | | 8/1980 | Bolick et al. | |
| 4,776,347 | A | | 10/1988 | Matthews | |

(Continued)

OTHER PUBLICATIONS

International Search Report and Written Opinion for PCT/US2011/023318 the counterpart application mailed on Oct. 13, 2011, 9 pages.

(Continued)

*Primary Examiner* — Pedro Philogene
*Assistant Examiner* — Lynnsy Summitt
(74) *Attorney, Agent, or Firm* — Sorell Lenna & Schmidt LLP

(57) ABSTRACT

A retractor system for percutaneous surgery in a patient includes first and second retractor portions positionable opposite one another in an incision of the patient. The system also includes at least one actuating member operable to provide an oscillating motion to at least one of the first and second retractor portions. The actuating member is in communication with a controller and is responsive to the controller to move and adjust at least one of the first and second retractor portions between a first position and a second position. The system also includes at least one pressure sensor and display and at least one timing circuit with display. In another form, a method is directed to retracting tissue for percutaneous access to a surgical site in a patient using the pressure sensors and display as will as the timing circuit and display to assure that the amount of pressure applied and the duration does not exceed pre-determined values.

22 Claims, 11 Drawing Sheets

(56) References Cited

U.S. PATENT DOCUMENTS

| | | | |
|---|---|---|---|
| 4,829,985 A * | 5/1989 | Couetil | A61B 17/0206 600/232 |
| 4,852,552 A * | 8/1989 | Chaux | A61B 17/0206 600/232 |
| 4,887,608 A | 12/1989 | Mohl et al. | |
| 4,928,700 A * | 5/1990 | Harada | A61B 5/021 600/485 |
| 4,945,896 A | 8/1990 | Gade | |
| 5,052,373 A * | 10/1991 | Michelson | A61B 17/0206 600/217 |
| 5,127,902 A | 7/1992 | Fischell | |
| 5,363,841 A * | 11/1994 | Coker | A61B 17/0206 600/211 |
| 5,365,921 A * | 11/1994 | Bookwalter | A61B 17/0206 269/261 |
| 5,749,853 A * | 5/1998 | O'Donnell | A61M 25/1018 604/97.03 |
| 5,769,781 A * | 6/1998 | Chappuis | A61B 17/02 600/201 |
| 5,865,731 A * | 2/1999 | Lenox | A61B 17/0206 600/232 |
| 5,902,233 A * | 5/1999 | Farley | A61B 17/0206 600/213 |
| 6,309,349 B1 * | 10/2001 | Bertolero | A61B 1/313 600/210 |
| 6,663,562 B2 * | 12/2003 | Chang | A61B 17/0206 600/213 |
| 6,916,294 B2 * | 7/2005 | Ayad | A61B 5/031 600/587 |
| 7,325,458 B2 | 2/2008 | Perlin | |
| 7,473,222 B2 * | 1/2009 | Dewey | A61B 17/0206 600/210 |
| 7,524,285 B2 * | 4/2009 | Branch | A61B 17/0206 600/214 |
| 7,666,136 B2 * | 2/2010 | Royse | A61B 17/0206 600/227 |
| 7,775,974 B2 * | 8/2010 | Buckner | A61B 1/32 600/202 |
| 8,226,554 B2 * | 7/2012 | McBride | A61B 1/32 600/201 |
| 2005/0215866 A1 | 9/2005 | Kim et al. | |
| 2005/0234304 A1 * | 10/2005 | Dewey | A61B 17/0206 600/210 |
| 2007/0198062 A1 * | 8/2007 | Miles | A61B 5/0488 607/2 |
| 2008/0033251 A1 | 2/2008 | Araghi | |
| 2008/0114209 A1 * | 5/2008 | Cohen | A61B 17/0206 600/210 |
| 2008/0132764 A1 * | 6/2008 | Hamada | A61B 17/02 600/201 |
| 2009/0018399 A1 * | 1/2009 | Martinelli | A61B 5/0488 600/210 |
| 2009/0036746 A1 * | 2/2009 | Blackwell | A61B 17/0206 600/219 |
| 2009/0259107 A1 * | 10/2009 | Crenshaw | A61B 5/0051 600/202 |
| 2009/0306480 A1 * | 12/2009 | Protopsaltis | A61B 17/0206 600/219 |
| 2010/0081885 A1 * | 4/2010 | Wing | A61B 17/0206 600/215 |
| 2011/0034779 A1 * | 2/2011 | Louftus | A61B 17/0206 600/210 |
| 2011/0098537 A1 * | 4/2011 | Justis | A61B 17/0206 600/210 |
| 2011/0184245 A1 * | 7/2011 | Xia | A61B 17/0206 600/202 |

OTHER PUBLICATIONS

Kawaguchi, et al. "Back Muscle Injury After Posterior Lumbar Spine Surgery: Topographic Evaluation of Intramuscular Pressure and Blood Flow in the Porcine Back Muscle During Surgery" Spine Journal, Nov. 15, 1996—vol. 21—Issue 22—pp. 2683-2688, Abstract.

Fischer, et al. "An Intra-Operative System for Relating Ischemic Damage to Retraction Forces" Poster, Complex Medical Engineering, May 2005.

Kwan, et al., "The Time Effect of Pressure on Tissue Viability: Investigation Using an Experimental Rat Model" Department of Health Technology and Informatics, Department of Applied Biology and Chemical Technology, and Department of Rehabilitation Sciences, The Hong Kong Polytechnic University, Hong Kong SAR, China, 2007.

Branch, et al., "MAST QUANDRANT Retractor System", Medial Lateral Blades Procedural Solutions Technique, Medtronic Sofamor Danek USA, Inc., 2009.

* cited by examiner

SURGICAL RETRACTOR INSTRUMENT SYSTEMS AND METHODS OF USING THE SAME

BACKGROUND

The present application relates to systems and methods for performing tissue retraction to facilitate a procedure, such as minimally invasive surgery, within in a patient.

Traditional surgical procedures for pathologies located within the body can cause significant trauma to the intervening tissues. These procedures often require a long incision, extensive muscle stripping, prolonged retraction of tissues, denervation and devascularization of tissue. Retraction of soft tissue using excessive pressure/tension and/or for extended periods of time can lead to tissue necrosis and/or extended postoperable recovery. That is, retraction using excessive pressure/tension for extended periods of time can lead to several weeks of post-operative recovery time due to the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. However, these minimally invasive surgical techniques may still result in damage to the tissue being retracted. Thus, while developments in minimally invasive surgery are steps in the right direction, there remains a need for further development in minimally invasive surgical instruments and methods.

SUMMARY OF THE INVENTION

The present invention is directed to a retractor having both pressure sensor for sensing the amount of pressure being applied to a surgical area by the retractor as well as a timer that measures the amount of time that the measured pressure is being applied in a surgical procedure. It has been found that the combination of the amount of pressure placed on cells using a retractor and the duration in which the pressure is applied has a direct correlation on the extent of localized cell necrosis and the amount of recovery time necessary after a procedure. That is, patients undergoing surgical procedures that use retractors that apply excess amounts of pressure for an extended period of time require more recovery time, have more localized cell necrosis around the area in which the retractor is used, and sustain more bruising and scarring around the area that can lead to additional pain for patients even after recovery. Therefore, one objective of the present invention, as further described below, is to provide a retractor that measures the amount of pressure and the amount of time in which the pressure is applied to a patient by a retractor in a surgical procedure so that it can be communicated to the surgeon or relayed to a controller. This way either the surgeon can consciencenously reapply the retractor once a predetermined threshold is reached or the controller can change the pressure in order to avoid the complications discussed above.

One nonlimiting embodiment of the present application is directed to a retractor system for percutaneous surgery in a patient that includes a first retractor portion including a proximal end and a distal end positionable in an incision and a second retractor portion including a proximal end and a distal end positionable in the incision opposite the first retractor portion wherein the first and second retractor portions define a first axis extending therebetween. The system also includes at least one actuating member operable to provide a first linear or oscillating motion to at least one of the first and second retractor portions, and a controller in communication with the at least one actuating member. A controller in communication with the actuating member is provided which is responsive to the controller so as to cause movement of the at least one of said first and second retractor portions between a first position and a second position. The system also includes at least one pressure sensor for actuating sensing pressure applied to tissue being retracted and for generating a sensor signal representative of the pressure. The sensor signal is received by a transponder in communication with the pressure sensor and converts the sensor signal to a pressure signal representative of the pressure. This signal is displayed for easy viewing by the surgeon using the device so that the surgeon could make the decision to maintain the pressure or move the retractor to a new position to reduce the negative affects associated with excessive retractor pressure on cells.

In another embodiment of the present invention, the retractor system further comprises a timing circuit in communication with at least one pressure sensor. The timing circuit is configured to begin timing upon the generation of a sensor signal representative of the pressure from the at least one pressure sensor and stop timing upon the cessation of the sensor signal representative of the pressure from the at least one pressure sensor.

Another embodiment of the present is directed to a method for retracting tissue for percutaneous access to a surgical site in a patient using any one of the retractor systems of the present invention. The method comprises positioning the retractor system of the present invention so that the first and second retractor portions relative to each other along the axis are in an open configuration to provide a working channel there between. Positioning the retractor into a incision and moving at least one of the first and second retractor portions between a first position and a second position so as to apply pressure to tissue positioned between the working channel. Measuring and displaying the pressure applied to tissue positioned between the working channel using a pressure sensor and a pressure gauge/display. Measuring and displaying the amount of time the pressure is applied to the retracted tissue using the timing circuit with display. Detecting the readings of the applied pressure and/or time and adjusting the first and second retractor portions between a first position and a second position if the readings indicate that either the pressure applied by the retractor, the time in which the pressure is applied, or both are above a pre-determined value. In one embodiment of the present invention, the pressure and time are not displayed but relayed to a controller and it is the controller that indicates the situation to the surgeon or automatically adjusts the retractor to avoid unfavorable pressures being reached for extended periods of time. In this embodiment displays showing the pressure and time on the retractor itself may not be necessary.

Another embodiment of the present application is a unique system for percutaneous surgery in a patient. Other embodiments include unique methods, systems, devices, kits, assemblies, equipment, and/or apparatus involving a retractor.

Further embodiments, forms, features, aspects, benefits, objects and advantages of the present application shall become apparent from the detailed description and figures provided herewith.

DESCRIPTION OF THE ILLUSTRATED EMBODIMENTS

Figure 1:
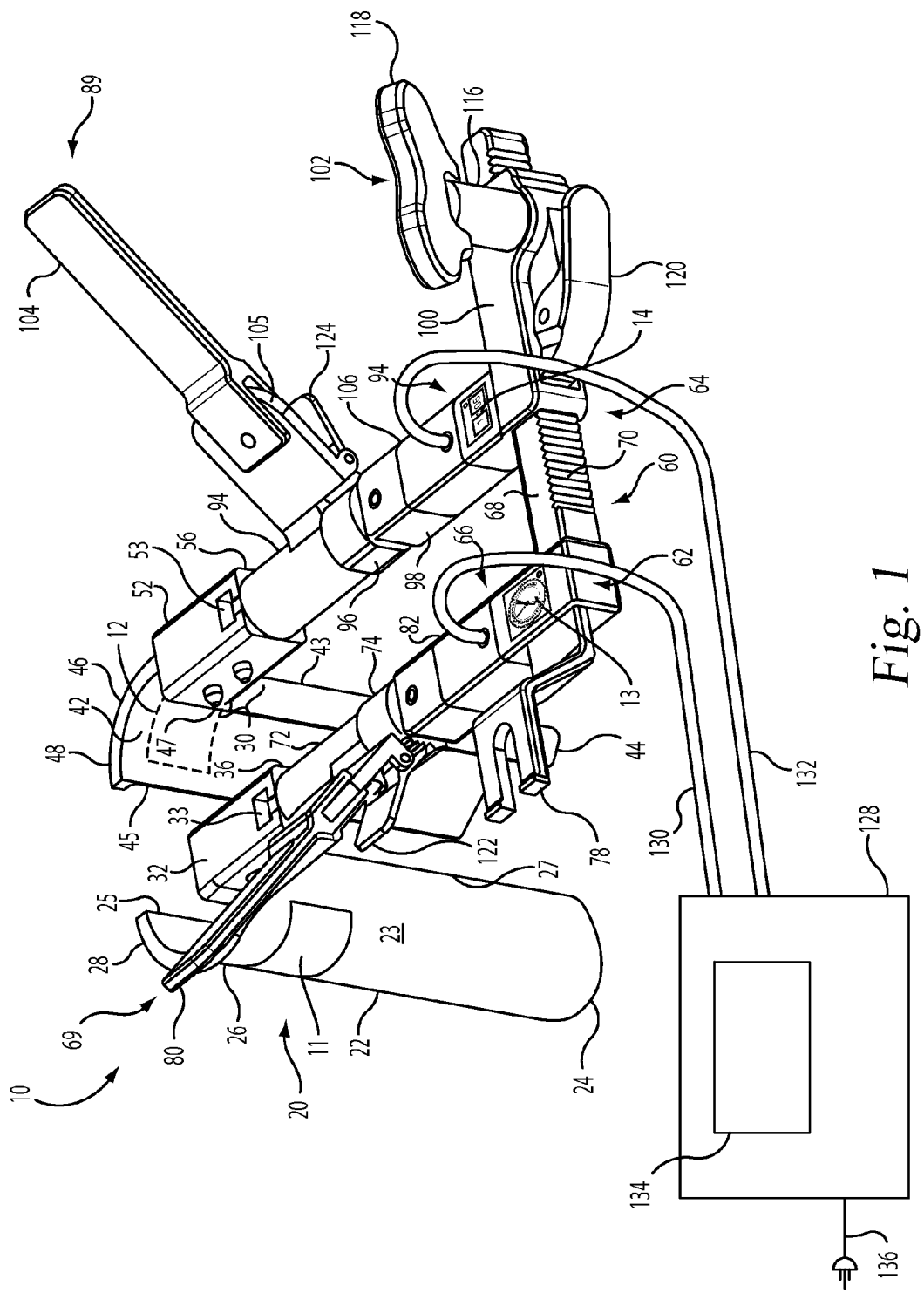
FIG. 1 is a perspective view of one embodiment of the retractor system having a pressure and time display.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Instruments and methods for performing percutaneous surgery, including spinal surgeries that include one or more techniques such as laminotomy, laminectomy, foramenotomy, facetectomy, discectomy, interbody fusion, spinal nucleus or disc replacement, and implant insertion including plates, rods, and bone engaging fasteners, for example, are provided. The surgery is performed through a working channel or passageway through skin and tissue of the patient provided by a retractor system which includes a retractor. Viewing of the surgical site at the working end of the retractor can be accomplished with viewing instruments mounted on the retractor, positioned over the retractor, positioned in other portals in the body, and/or through a viewing system such as lateral fluoroscopy. The retractor is movable in situ to increase the size of the working channel to facilitate access to the working space at the distal end of the retractor while minimizing trauma to tissue surrounding the retractor.

In one embodiment of the present invention a retractor system of the is provided with a pressure/tension sensor and/or a timer that measures the amount of pressure/tension applied to the soft tissue by the retractor as well as the duration in which it is applied. The sensor/timer is attached to a display that displays the reading taken by the sensor/timer. This sensor system can be used with any standard retractor device or in particular with a retractor system having oscillating motion. In particular, one form of retraction system that may be equipped with a pressure/tension sensor and/or timer has at least one actuating member and is operable to oscillate at least a portion of the retractor between first and second positions relative to the surrounding tissue and skin, although other forms for providing an oscillating motion of the retractor relative to the surrounding tissue and skin are provided. The retractor can be used with any surgical approach to the spine, including anterior, posterior, posterior mid-line, lateral, postero-lateral, and/or antero-lateral approaches, and in other regions besides the spine.

In one embodiment of the present invention, the pressure/tension sensor as well as the timer is/are connected to one or more displays. The display(s) is/are positioned on the retractor so that the surgeon using the retractor can easily view the display(s). In one embodiment of the invention, two different displays are provided. One display shows the amount of pressure being applied by the retractor and a second display shows the duration of time in which the pressure is being applied.

The pressure display can either be digital or as a color-coded/needle display. In particular, one type of color-coded display that can be used is the standard dial having a pointer that travels on a pivot point from left to right. The face of the pressure display in which the dial pivots above can be color-coded with green, yellow and red colors. Green indicating that the pressure applied is within acceptable levels; yellow indicating that the pressure being applied is approaching unfavorable levels; and red indicating that the pressure being applied by the retractor exceeds recommended levels and can lead to cell necrosis, extended recovery periods, scarring as well as other potential complications.

As indicated above, applying pressure, even if it is within the safe range, for extended periods of time can also cause complications and extended recovery time. For this reason the retractor of the present invention is also equipped with a timer having a display that is in communication with the pressure sensors. Once one or both of the pressure sensors sense pressure being applied to tissue being retracted, a signal is sent to the timer to begin timing. The elapsed time is displayed on a display positioned on the retractor (or in close proximity) so that it is in clear site of the surgeon. The surgeon can use the elapsed time display to determine whether the retractor should be moved or can remain in place without causing any of the detrimental effects discussed above.

The timer display can be digital, a color coded dial display or a meter that indicates that the elapsed time in which the pressure/tension is being applied to tissue being retracted. In the alternative, the time display can be equipped with a programmable audible device or light that sounds or activates once the elapsed time enters into a pre-determined caution zone. The light signal and/or audible signal can intensify or change colors when the elapsed time approaches detrimental levels. In one embodiment of the present invention, the retractor is equipped with a single integrated pressure and time display that provides information not only about the pressure and time individually but also as an integrated function.

The embodiments of the present invention are further described below in connection with the FIGS. 1-8.

Figure 2:
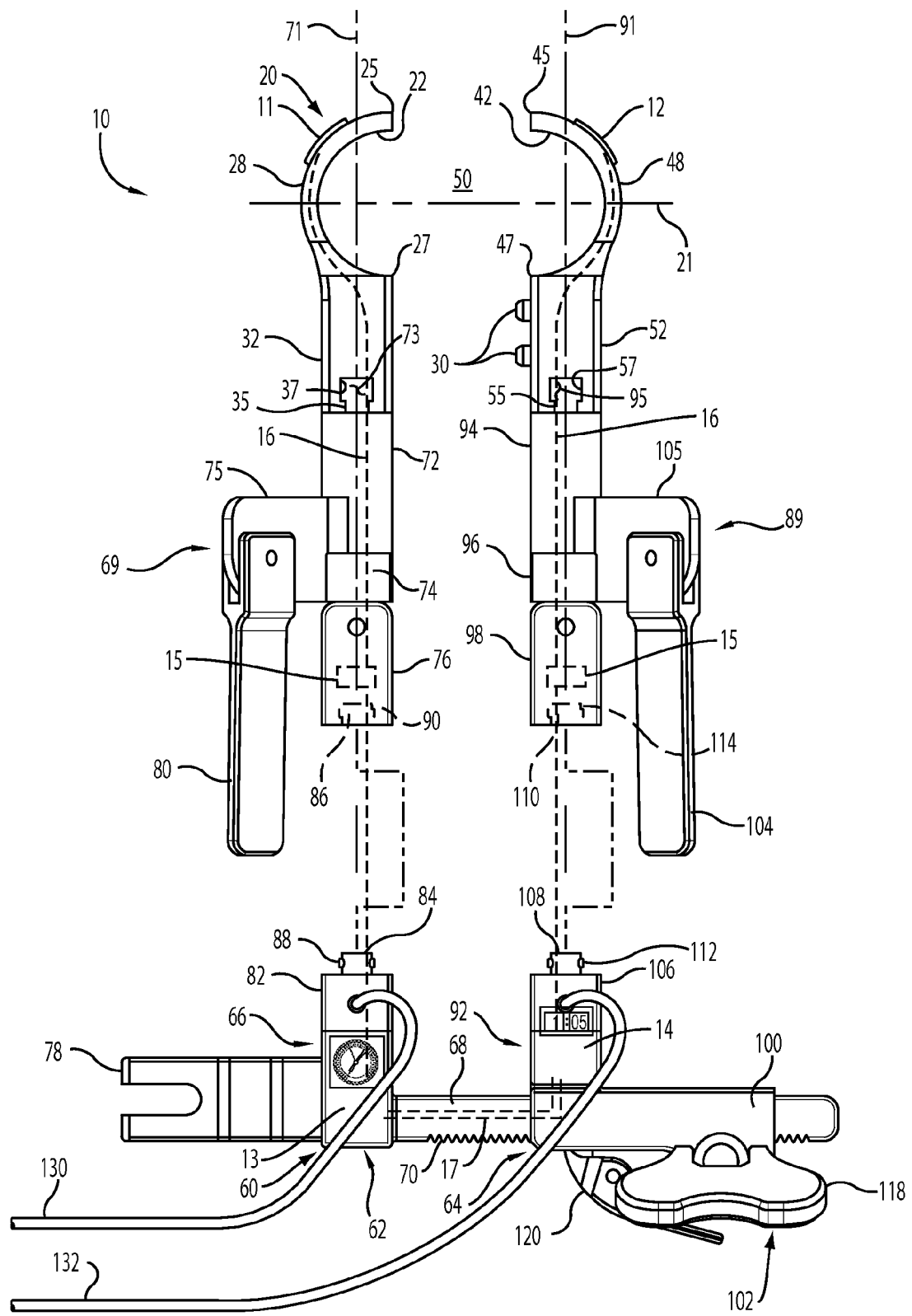
FIG. 2 is a partially exploded plan view of the retractor system in FIG. 1.
Figure 3:
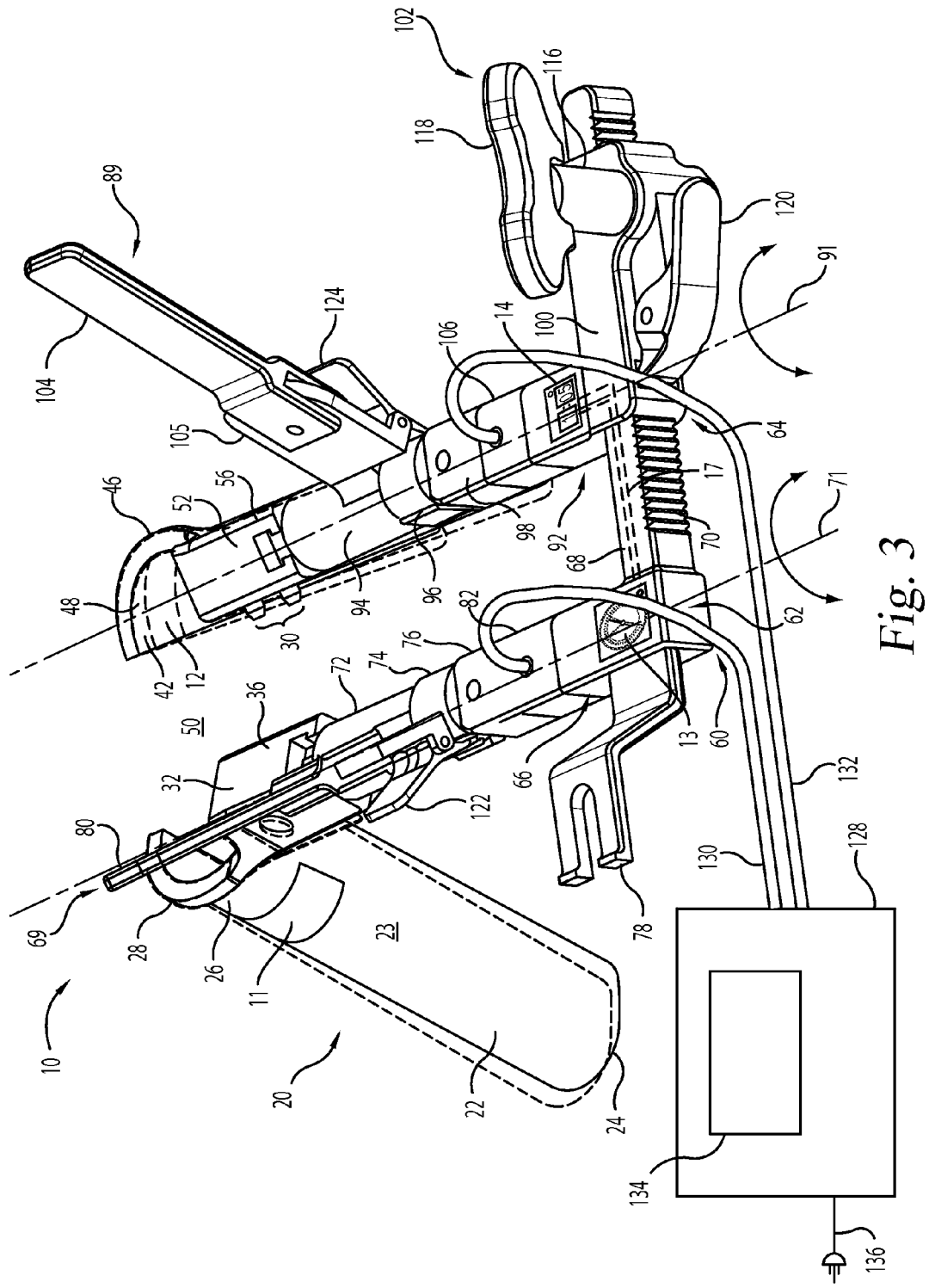
FIG. 3 is a perspective view of the retractor system of FIG. 1 illustrating the retractor portions pivoted and an oscillating motion of the retractor portions.

Referring generally to FIGS. 1-3, there is illustrated one embodiment retractor system 10 which includes a retractor 20 in an expanded configuration. Retractor 20 includes a first retractor portion 22 and a second retractor portion 42. First retractor portion 22 is generally in the form of a retractor blade and includes a body 23 extending between a distal end 24 and an opposite proximal end 26. Second retractor portion 42 is also generally in the form of a retractor blade and includes a body 43 extending between a distal end 44 and an opposite proximal end 46. The first retractor portion 22 and the second retractor portion 42 are equipped with a first pressure sensor 12 and a second pressure sensor 11, respectively. The first and second pressure sensors 11,12 are designed and positioned on the first and second retractor portions 22, 42 so as to detect pressure being applied on the first and second retractor portions 22, 42. The pressure are connected to a transponder 15 that converts sensor signals from the sensors to a pressure signal representative of the pressure applied on pressures sensors 11 and 12 by the retractor. The transponder 15 is in communication with a pressure gauge 13, further discussed below, that displays the pressure reading for the surgeon.

In the expanded configuration illustrated in FIGS. 1-3, a working channel 50 is formed between first retractor portion 22 and second retractor portion 42. Working channel 50 extends between and opens at distal ends 24, 44 and proximal ends 26, 46. While not illustrated, it should be appreciated that first retractor portion 22 and second retractor portion 42 may brought adjacent one another to an insertion configuration to more readily facilitate insertion of retractor 20 into an incision made in the skin. For example, first retractor portion 22 can be positioned adjacent to or mated with second retractor portion 42 along adjacent ones of the longitudinal edges 25, 27 of first retractor portion 22 and longitudinal edges 45, 47 of second retractor portion 42, although other arrangements between the adjacent edges are also contemplated. It is further contemplated that the longitudinal edges can be spaced from one another in the insertion configuration. In addition, distal ends 24, 44 can be beveled or distally tapered to facilitate insertion, although non-beveled ends are also contemplated.

Retractor 20 is insertable through skin and tissue of a patient to provide working channel 50 to the surgical site. It is contemplated that retractor 20 is inserted through the skin and tissue in an insertion configuration for working channel 50 as described above. In the insertion configuration, working channel 50 is substantially enclosed or circumscribed by first retractor portion 22 and second retractor portion 42. After insertion into the patient, working channel 50 can be enlarged by separating first retractor portion 22 and second retractor portion 42 away from one another along an axis 21 extending therebetween. Separation of first and second retractor portions 22, 42 increases the size of working channel 50 from proximal ends 26, 46 to distal ends 24, 44 and puts pressure on pressure sensors 11 and/or 12.

As stated above, retractor 20 is equipped with a pressure gauge 13 located on the body of the retractor 20. The gauge 13 displays the pressure reading being transmitted by pressure sensors 11 and 12 thought the transponders 15. In the exemplary embodiment shown in the figures, the pressure gauge 13 is located on or near the first connection assembly 62 of the first extension arm 66 and is in communication with the pressure sensors 11 and 12. The pressure gauge 13 may be in different forms such as digital a read out, light coded readout or a colored dial display. For exemplary purposes only, pressure gauge 13 is shown as a color-coded dial display having colors located on the dial that indicates safe, cautionary, and detrimental pressure conditions. Although any colors can be used on the faceplate of the pressure gauge 18A (See FIG. 1A), it is preferred that the colors used to show the different levels of pressure being applied by the retractor to the skin are the universal colors green for safe pressure, yellow for cautious pressure levels and red for detrimental pressure levels being applied. As discussed above this display can be used by the surgeon to determine whether the retractor has to be repositioned so as to avoid complications and extended recovery periods.

Figure 1A:
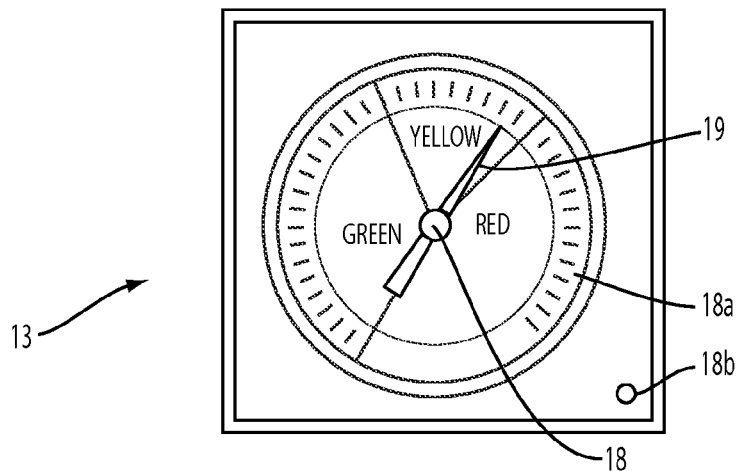
FIG. 1A is expanded view of the pressure sensor.
Figure 1B:
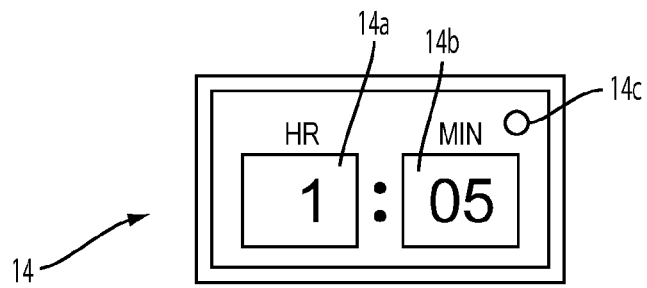
FIG. 1B is expanded view of the time display.

The pressure gauge 13 is further shown in FIG. 1A. As shown, the pressure gauge 13 has a dial 19 that pivots on a pivot point 18 above a faceplate 18a. The faceplate 18a is shown with markings along the perimeter that correspond to particular pressure measurements and is divided into three color-coded regions namely, green, yellow and red. Pressure gauge 13 can also be equipped with a indicator light 18b that lights up green when dial 19 is in the green zone, indicating that the pressure applied to the retracted tissue is within acceptable levels; lights up yellow when dial 19 is in the yellow zone, indicating that the pressure applied is reaching unacceptable levels; and lights up red when dial 19 is in the red zone which indicates that the pressure being applied by the retractor 20 is detrimental to the retracted tissue and action should be taken. The light system is designed to provide a quick reference for the surgeon without diverting the surgeon's attention away from the surgical procedure.

Similarly, as discussed above, as applying excess pressure to retracted tissue can have detrimental effects on retracted tissue, applying pressure to retracted tissue for extended periods of time can also lead to cell death and longer recovery periods. Accordingly, one embodiment of retractor 20 of the present invention is equipped with a timer having a display 14. As with the pressure gauge 13, the timer with display 14 is located on the body of the retractor 20. In the exemplary embodiment shown in the figures, the timer having a display 14 is located on or near the second connection assembly of the second extension arm 94 but in alternative embodiments can be located external to retractor 20. The timer with display 14 is in communication with pressure sensors 11 and 12 and time can be displayed in analog or digital format. For exemplary purposes only, the timer display 14 is shown as a digital readout, however other types of readouts can be used. As discussed above, the display helps the surgeon to determine whether the amount of time that the retractor 20 is in place is acceptable or if retractor 20 has to be repositioned in order to avoid the negative aspects associated with applying pressure to tissue for extended periods of time.

In one embodiment of the present invention the timer display 14 has a hours column 14a, a minutes column 14b and a indicator light 14c. The indicator light 14c can be used as a fast reference for the surgeon to determine if the amount of time the retractor 20 is in place is acceptable or not. For example, if the amount of time that retractor 20 is in place is less than a predetermined value, the light would indicate green. Should the time surpass this predetermined value and enter into a cautionary period, the light would read as yellow. Finally, if the time elapsed surpasses a pre-determined unacceptable value, then the light would read as red. Various light patterns can be used to indicate that the next level is approaching such as, blinking just before going from a safe level to a cautionary level and/or from a cautionary level to an undesired level. Still further, an audible indicator can be included in the timer display 14 that sounds as the elapsed time approaches or reaches undesired levels so as to alert the surgeon. In yet another embodiment of the present invention, the pressure sensor and time circuit can also be attached to the controller and once an unfavorable pressure, time of pressure applied or combination of both time and pressure is reached the control display such information so that the surgeon can take the proper action. Depending on the placement of the retractor, short periods of low or high pressure may be acceptable but long periods of relatively low pressure may lead to localized cell necrosis, scaring and extended recovery periods. For this reason it is important to measure an integrated pressure-time value below which it is important to stay in order to prevent damage to soft tissues.

Figure 1C:
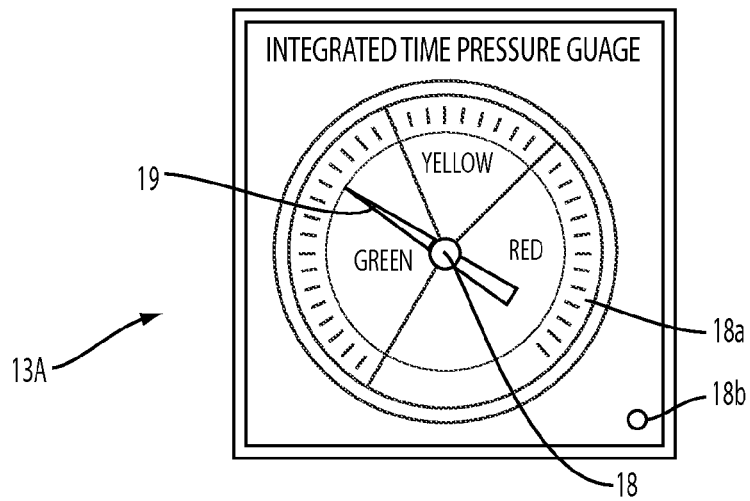
FIG. 1C is expanded view of an integrated pressure/time display.

As mentioned above, the pressure sensors 11, 12 can be in communication with a transponder 15 and then with the pressure gauge 13 and timer display 14. In one embodiment of the present invention the retractor is equipped with a single integrated pressure/time gauge as shown in FIG. 1C that indicates that the integrated pressure/time being applied by the retractor is acceptable, reaching unacceptable levels or is unacceptable. This gauge integrates the time and pressure and displays it as a single reading so that the surgeon does not have to pay attention to time and pressure separately. Integrated time/pressure gauge 13A includes a dial 19 that pivots on a pivot point 18 above a faceplate 18a. The faceplate 18a is shown with markings along the perimeter that correspond to particular integrated pressure/time measurements and is divided into three color-coded regions namely, green, yellow and red. Pressure gauge 13a can also be equipped with a indicator light 18b that lights up green when dial 19 is in the green zone, indicating that the combination of time and pressure applied to the retracted tissue is within acceptable levels; lights up yellow when dial 19 is in the yellow zone, indicating that the combination of time and pressure applied is reaching unacceptable levels; and lights up red when dial 19 is in the red zone which indicates that the combination of time and pressure being applied by the retractor 20 is detrimental to the retracted tissue and action should be taken. The light system is designed to provide a quick reference for the surgeon without diverting the surgeon's attention away from the surgical procedure.

Figure 1D:
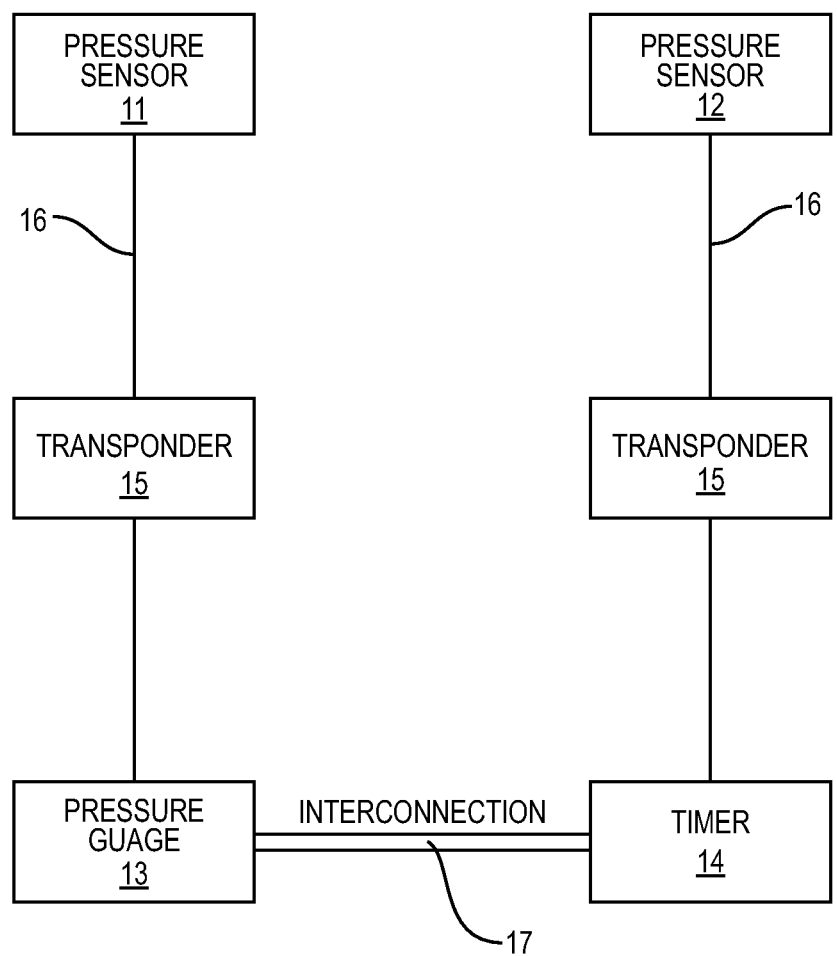
FIG. 1D is a circuit flow chart of the sensors and displays.
Figure 1E:
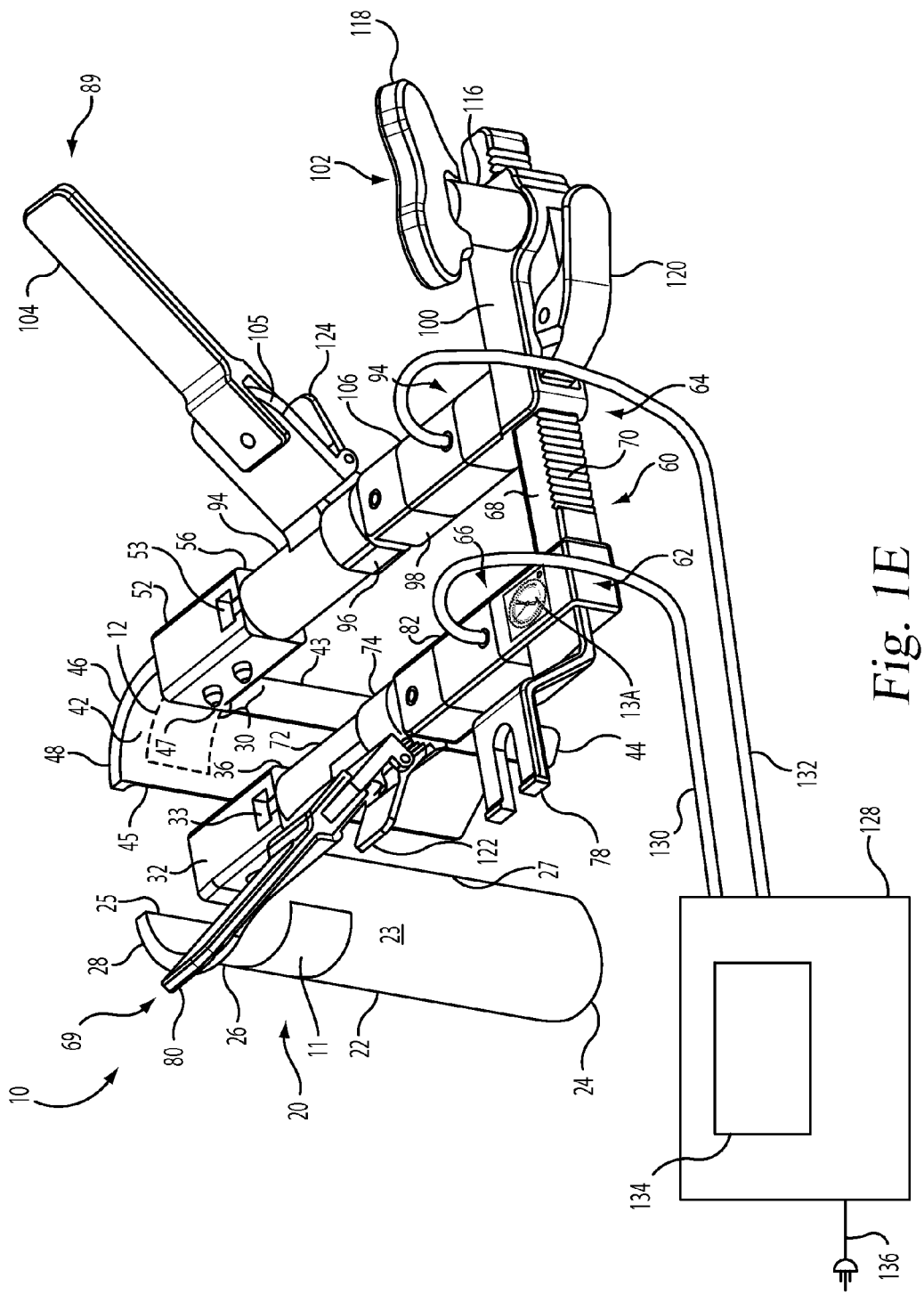
FIG. 1E is a perspective view of one embodiment the retractor system having an integrated pressure/time display.

FIG. 1D shows the retractor with the integrated gauge 13a. The integrated display 13a has all the features of the pressure display including color indicia and a FIG. 1E includes a flow chart that briefly describes the connectivity of these components in order to have the pressure signals and time elapsed properly displayed. It is understood that the pressure display and timer with display is positioned on the retractor but can be located on a separate panel or controller.

When retractor 20 is in the insertion configuration, working channel 50 is circumscribed or substantially enclosed by first retractor portion 22 and second retractor portion 42. Working channel 50 can have a size in the insertion configuration that allows passage of one or more surgical instruments and/or implants to the surgical location in the patient's body. It may be desirable during surgery to provide greater access to the surgical site in the patient's body beyond the locations provided through working channel 50 in its insertion configuration. First retractor portion 22 and second retractor portion 42 are movable away from one another to enlarge working channel 50. In the enlarged configuration of working channel 50, a space is formed between the adjacent longitudinal edges 25, 27 and 45, 47 of first retractor portion 22 and second retractor portion 42. The space between the adjacent longitudinal edges 25, 27 and 45, 47 exposes enlarged working channel 50 to skin and tissue of the patient between the separated first retractor portion 22 and second retractor portion 42. This exposed tissue can also be accessed by the surgeon through the enlarged working channel 50 with one or more instruments and/or implants. It is further contemplated that a shield, guard or tissue retractor could be placed in enlarged working channel 50 to maintain the exposed tissue away from the enlarged working channel 50.

Viewing instruments can be positioned in or adjacent to working channel 50 to facilitate surgeon viewing of the surgical site. For example, an endoscopic viewing element can be mounted on the proximal end of one of first and second retractor portions 22, 42 with a scope portion extending along working channel 50. A microscopic viewing element can be positioned over the proximal end of one of first and second retractor portions 22, 42 for viewing the surgical site. Other imaging techniques, such as lateral fluoroscopy, can be used alone or in combination with the endoscopic and microscopic viewing elements. It is further contemplated that other instruments can be mounted on the proximal end of one of first and second retractor portions 22, 42, such as nerve root retractors, tissue retractors, forceps, cutter, drills, scrapers, reamers, separators, rongeurs, taps, cauterization instruments, irrigation and/or aspiration instruments, illumination instruments, inserter instruments, and the like for use in surgical procedures through retractor 20 at the surgical site. Such viewing instruments and other instruments can be employed with working channel 50 in its initial insertion configuration and/or its enlarged configuration.

First retractor portion 22 has a perimeter length along distal end 24 which can be about the same as the perimeter length of first portion 22 at proximal end 26. Second retractor portion 42 includes a perimeter length along distal end 44 which can be about the same as the perimeter length of second retractor portion 42 adjacent proximal end 46. In the illustrated form, first retractor portion 22 includes body 23 with a semi-cylindrical shape extending between distal end 24 and proximal end 26 and second retractor portion 42 includes body 43 with a semi-cylindrical shape extending between distal end 44 and proximal end 46. In this arrangement, first and second retractor portions 22, 42 form a generally circular cross-section for working channel 50 when placed adjacent one another. Other cross-sectional shapes are also contemplated for first and second retractor portions 22, 42, such as, for example, any open sided polygonal shape, curved shape, or combined curved/polygonal shape. When first and second retractor portions 22, 42 are separated from one another, working channel 50 can have a cylindrical or frusto-conical shape with, for example, a cross-section that is oval, elliptical, circular, curved, polygonal, or combined polygonal/curved in shape.

First and second retractor portions 22, 42 can be provided with sufficient rigidity between their distal and proximal ends to separate and maintain separation of adjacent tissue when first and second retractor portions 22, 42 are initially inserted and also when the adjacent tissue is retracted by moving first retractor portion 22 and second retractor portion 42 away from one another. For example, first and second retractor portions 22, 42 can include a thickness which provides sufficient rigidity to resist bending or bowing under the forces exerted on it by the retracted tissue and/or muscle. Also, the semicircular shaped cross-section of first and second retractor portions 22, 42 can be configured to provide a sufficient section modulus or moment of inertia in the direction of movement of first and second retractor portions 22, 42 to resist bending, bowing and/or deflection forces applied during such movement.

A collar 28 extends about proximal end 26 of first retractor portion 22, and forms a lip extending about the outer surface of body 23. Similarly, a collar 48 extends about proximal end 46 of second retractor portion 42, and defines a lip extending about the outer surface of body 43. It is further contemplated that first and second retractor portions 22, 42 can be provided with or without a collar and/or a lip. First and second retractor portions 22, 42 can also be provided with bracket members for engagement with an external arm that supports retractor 20 while positioned in the patient.

Extending from collar 28 of first retractor portion 22 is a first engagement member 32 having a head portion 36 forming a recess 33 therein. Extending from collar 48 of second retractor portion 42 is a second engagement member 52 having a head portion 56 forming a recess 53 therein. Engagement members 32, 52 can be integrally formed with or removably engaged to the respective collars 28, 48. As discussed further below, an instrument for separating first retractor portion 22 and second retractor portion 42 can be non-releasably or releasably engaged to engagement members 32, 52 for application of a separation force to enlarge working channel 50 by separating first retractor portion 22 and second retractor portion 42. Such an instrument could also be releasably or non-releasably engaged to first retractor portion 22 and second retractor portion 42. Engagement members 32, 52 extend laterally from first and second retractor portions 22, 42 to facilitate engagement of a separation instrument to engagement members 32, 52 without obstructing working channel 50 with the separation instrument. Such an instrument could also maintain first retractor portion 22 and second retractor portion 42 in the initial insertion configuration during and after insertion. The separation instrument can also maintain the enlarged configuration for working channel 50 in situ.

Recesses 33, 53 are adapted to receive engagement arms of the separation instrument engageable to first and second retractor portions 22, 42. In the illustrated embodiments, engagement members 32, 52 extend laterally from and project proximally above the respective collar 28, 48. Engagement members 32, 52 extend alongside one another and abut one another when first and second retractor portions 22, 42 are in their insertion configuration. Other configurations for the engagement members are also contemplated, including engagement members that are non-linear, that extend in directions away from one another when first and second retractor portions 22, 24 are in their insertion configuration, and engagement members that do not abut one another in the insertion configuration.

Recesses 33, 53 open laterally to receive respective ones of the engagement arms of the separation instrument. Recess 33 includes a keyway opening 35 and a receptacle 37 in communication with opening 35. Receptacle 37 is enlarged relative to opening 35, and is shaped to receive a portion of the engagement arm of the separation instrument positioned therein. Similarly, recess 53 includes a keyway opening 55 and a receptacle 57 in communication with opening 55. Receptacle 57 is enlarged relative to opening 55, and is shaped to receive a portion of the engagement arm of the separation instrument positioned therein. Openings 35, 55 and receptacles 37, 57 are open along the proximal sides of the respective engagement members 32, 52 to facilitate placement of the separation instrument engagement arms therein. Other configurations for the recess 33, 53 are also contemplated, including recesses that are enclosed, uniform, or any other suitable configuration to receive a at least a portion of an engagement arm. Still other embodiments contemplate that engagement members 32, 52 do not include recesses, but rather are shaped for receipt in or otherwise engage the respective engagement arm of the separation instrument. In one or more other forms, it should be appreciated that engagement members 32, 52 may be engaged to the engagement arms of the separation instrument by dovetail connections, fasteners, threaded coupling members, clamping members, snap rings, compression bands, straps, ball-detent mechanisms, releasably interlocking cams or tabs, welding, fusing, and/or adhering, just to name a few possibilities.

As shown in FIGS. 1-3, alignment members 30 can be provided along one side of one of the engagement members 32, 52 (engagement member 52 in the illustrated embodiment). In the illustrated embodiment, alignment members 30 are rounded protrusions which are received in holes (not illustrated) provided in the adjacent side of the other engagement member 32, 52 when engagement members 32, 52 are positioned adjacent one another. Alignment members 30 maintain first retractor portion 22 and second retractor portion 42 in longitudinal alignment with one another during and after insertion. Other embodiments contemplate other arrangements for aligning and/or releasably coupling first retractor portion 22 and second retractor portion 42 to one another. Examples of such arrangements include dovetail connections, fasteners, threaded coupling members, clamping members, snap rings, compression bands, straps, ball-detent mechanisms, and releasably interlocking cams or tabs, just to provide a few possibilities.

Retractor 20 also includes a separation instrument 60 operable to move first and second retractor portions 22, 42 away from one another to enlarge working channel 50. It is contemplated that separation instrument 60 includes a lateral separator operable to linearly move first and second retractor portions 22, 42 away from one another along axis 21. It is further contemplated that separation instrument 60 includes at least one rotational separator to pivotally move distal ends 24, 44 of first and second retractor portions 22, 42 away from one another along axis 21, although embodiments where two rotational separators are present, as well as those where the at least one rotational separator is absent, are contemplated. The lateral and rotational separators can be selectively employed by the surgeon during the surgical procedure to enlarge working channel 50 and provide the tissue retraction desired for conducting the surgical procedure through working channel 50. Enlargement of working channel 50 can further retract tissue away from the surgical site distal of the distal ends of first and second retractor portions 22, 42 to provide greater access to tissue, bony structures, and other anatomical spaces located distally of retractor 20.

Separation instrument 60 includes a first connection assembly 62 movably coupled with a second connection assembly 64. First connection assembly 62 is further coupled to first retractor portion 22, and second connection assembly 64 is coupled to second retractor portion 42. First and second connection assemblies 62, 64 extend away from first and second retractor portions 22, 42 and away from the proximal end opening of working channel 50 to facilitate access to working channel 50 during the surgical procedure. First and second connection assemblies 62, 64 are operable to move first and second retractor portions 22, 42 toward and away from one another to separate tissue. First and second connection assemblies 62, 64 further include lever assemblies 69, 89, respectively, that are operable to rotate first and second retractor portions 22, 42 about their proximal ends to move their distal ends away from one another.

First connection assembly 62 includes a first engagement arm 72 coupled to first engagement member 32 of first retractor portion 22 and to a first intermediate member 74. First connection assembly 62 also includes a second intermediate member 76 which is releasably engageable with a first extension arm 66, although non-releasable but freely rotational engagement between intermediate member 76 and first extend arm 66 is also contemplated. A coupling arm 68 is transversely oriented to and extends from the end of first extension arm 66 opposite first engagement arm 72. A bracket member 78 extends from coupling arm 68, and is engageable by a flexible arm mounted to a surgical table, for example. First intermediate member 74 is fixedly coupled to second intermediate member 76. First engagement arm 72 is rotatable relative to first intermediate member 74. A first mounting member 75 extends from first engagement arm 72. A first lever arm 80 is pivotally mounted to first mounting member 75. As indicated above, second intermediate member 76 is releasably engaged with first extension arm 66. More particularly, first extension arm 66 includes an actuating member 82 positioned at the end thereof opposite coupling arm 68. Actuating member 82 includes a rectangular or otherwise keyed shaft 84 that is received in receptacle 86 positioned on the end of second intermediate member 76. In the illustrated form, shaft 84 includes spring-biased ball mechanisms 88 that are received in corresponding detents 90 of receptacle 86 to releasably couple actuating member 82 to second intermediate member 76, although it should be appreciated that other arrangements for coupling these elements are also contemplated. In one form, actuating member 82 may be provided as an electric, pneumatic or hydraulic motor that rotates shaft 84, although other types of actuators are also contemplated, including for example mechanical vibrators and ultrasonic motion generators. Similarly, actuating member 82 is operable to rotate second intermediate member 76 in an oscillating motion between first and second positions about axis 71, further details of which will be provided below. As second intermediate member 76 is oscillated, first intermediate member 74, first engagement arm 72 and first engagement member 32 are oscillated in a similar fashion about axis 71. Similarly, proximal end 26 of first retractor portion 22 is also rotated about axis 71 such that its distal end 24 is moved back and forth relative to second retractor portion 42. However, it should be appreciated that first connection assembly 62 is not rotated between coupling arm 68 and actuating member 82.

Second connection assembly 64 includes a second engagement arm 94 coupled to second engagement member 52 of second retractor portion 42 and to a third intermediate member 96. Second connection assembly 64 also includes a fourth intermediate member 98 which is releasably engageable with a second extension arm 92, although non-releasable but freely rotational engagement between intermediate member 98 and second extend arm 94 is also contemplated. A housing 100 extends from the end of second extension arm 92 opposite second engagement arm 94. Housing 100 includes a passage through which coupling arm 68 is movably received. An adjustment mechanism 102 mounted to housing 100 is engageable to coupling arm 68 and operable to translate coupling arm 68 in housing 100 to effect movement of first and second retractor portions 22, 42 toward and away from one another along translation axis 21. Third intermediate member 96 is fixedly coupled to fourth intermediate member 98. Second engagement arm 94 is rotatable relative to third intermediate member 96. A second mounting member 105 extends from second engagement arm 94. A second lever arm 104 is pivotally mounted to second mounting member 105. As indicated above, fourth intermediate member 98 is releasably engaged with second extension arm 92. More particularly, second extension arm 92 includes an actuating member 106 positioned at the end thereof opposite coupling arm 68. Actuating member 106 includes a rectangular or otherwise keyed shaft 108 that is received in receptacle 110 positioned on the end of fourth intermediate member 98. In the illustrated form, shaft 108 includes spring-biased ball mechanisms 112 that are received in corresponding detents 114 of receptacle 110 to releasably couple actuating member 106 to fourth intermediate member 98, although it should be appreciated that other arrangements for coupling these elements is also contemplated. In one form, actuating member 106 may be provided as an electric, pneumatic or hydraulic motor that rotates shaft 108, although other types of actuators are also contemplated, including for example mechanical vibrators and ultrasonic motion generators. Similarly, actuating member 106 is operable to rotate fourth intermediate member 98 in an oscillating motion between first and second positions about axis 91, further details of which will be provided below. As fourth intermediate member 98 is oscillated, third intermediate member 96, second engagement arm 94 and second engagement member 52 are oscillated in a similar fashion about axis 91. Similarly, proximal end 46 of second retractor portion 42 is also rotated about axis 91 such that distal end 44 is moved back and forth relative to first retractor portion 22. However, it should be appreciated that second connection assembly 64 is not rotated between coupling arm 68 and actuating member 103. In addition, in one or more non-illustrated forms, it should be appreciated that only one of first connection assembly 62 and second connection assembly 64 may be provided with an actuating member.

In the illustrated embodiment, coupling arm 68 includes a number of ratchet teeth 70 formed therealong, which are engageable by adjustment mechanism 102. Adjustment mechanism 102 includes a gear wheel 116 with teeth that interdigitate with teeth 70 to effect movement of coupling arm 68 in housing 100 as handle 118 is rotated. A locking mechanism 120 is spring-biased into engagement with teeth 70, and maintains separation of first and second retractor portions 22, 42 when handle 118 is released. Locking mechanism 120 can also be depressed to pivot its engagement end out of engagement with teeth 70 and allow first and second retractor portions 22, 42 to move toward one another.

As shown in FIG. 2 for example, first and second engagement arms 72, 94 include feet 73, 95, respectively. Feet 73, 95 are slidably and removably received in respective ones of the recesses 33, 53 of engagement members 32, 52. In the illustrated embodiment, feet 73, 95 include an enlarged outer end portion and a smaller cross-section intermediate transition portion extending between engagement arms 72, 94 and the enlarged outer end portions. The intermediate transition portions are received in the intermediate keyway openings 35, 55, and the enlarged outer end portions are received in receptacles 37, 57.

Feet 73, 95 are received in recesses 33, 53 in such a manner that, as discussed further below, lever arms 80, 104 can effect pivoting of first and second retractor portions 22, 42 by rotating engagement arms 72, 94 about their respective axes 71, 91, respectively. Furthermore, separation instrument 60 can be easily removed from first and second retractor portions 22, 42, facilitating clean-up of the instrument assembly after the surgical procedure. It is also contemplated that disposable first and second retractor portions 22, 42 may be used, or that a set of first and second retractor portions 22, 42 can be provided in various lengths, shapes and/or sizes from which a surgeon may select and employ with separation instrument 60.

First and third intermediate members 74, 96 each include a locking portion that is engageable with a respective one of lever arm locking assemblies 122, 124. Lever arm locking assemblies 122, 124 each include a pawl pivotally coupled to an adjacent one of the mounting members 75, 105. Intermediate members 74, 96 each include engagement portions to which the locking assemblies 122, 124 are engageable to maintain a pivoted position of first and second the portions 22, 42. For example, as illustrated in FIG. 3, first and second the portions 22, 42 have been rotated about axes 71, 91, respectively, relative to the arrangement illustrated in FIG. 1. Similarly, locking assemblies 122, 124 engage with intermediate members 74, 96 to maintain the relative rotational positioning of first and second retractor portions 22, 42. As would be appreciated by those skilled in the art, this arrangement allows distal ends 24, 44 of first and second retractor portions 22, 42 to be pivoted away from one another, and maintained in their pivoted positions, to provide working channel 50 with a tapered configuration that reduces in size from the distal ends of first and second retractor portions 22, 42 through the skin to the proximal ends of first and second retractor portions 22, 42. A tapered working channel provides the surgeon greater access and increased visualization of the surgical site while minimizing tissue retraction. The tapered working channel 50 also allows greater angulation of instruments and implants placed through working channel 50, more selection in positioning of instruments and implants within working channel 50, and the ability to position instruments and implants adjacent the inner wall surfaces of the separated first and second portions 22, 42, increasing the room available at the surgical site for multiple instruments and for orienting implants. Further details regarding the pivotal arrangement of first and second retractor portions 22, 42, as well as various other features described above with respect to retractor 20, may be found in U.S. Pat. No. 7,473,222, the contents of which are incorporated herein by reference in their entirety. In addition, in one or more non-illustrated forms, separation instrument 60 may not include the rotational separators on first and second connection assemblies 62, 64, and actuating members 82, 106 may be used to rotate first and second retractor portions 22, 42 as appropriate in addition to providing the oscillating motion mentioned above and discussed in further detail below.

Retractor system 10 also includes a controller 128 that is connected by pathways 128, 130 to actuating members 82, 106, respectively, such that controller 128 and actuating members 82, 106 are in communication with one another. While controller 128 is positioned remotely to actuating members 82, 106 in the illustrated form, it should be appreciated that each of actuating members 82, 106 could be provided with its own, integrated controller. Moreover, in one or more alternative forms, it should be appreciated that retractor system 10 may be provided with a wireless communication interface between controller 128 and one or both of actuating members 82, 106. In addition, while pathways 130, 132 are both directly coupled to the exterior of actuating members 82, 106, it should be appreciated that in alternative forms pathways 130, 132 may be positioned within one or both of first connection assembly 62 and second connection assembly 64. Controller 128 includes a user interface 134 which may include a touch-screen, switches, buttons, levers, keypad, keyboard and/or mouse, just to name a few possibilities, with which a user can provide an actuation command to controller 128. In another form, it is contemplated that user interface 134 and controller 128 are configured to facilitate voice activation and control of system 10. In response to the actuation command, actuating members 82, 106 rotate shafts 84, 108 in an oscillating fashion to provide a desired rotation of first and second retractor portions 22, 42 about their proximal ends 26, 46 and of distal ends 24, 44 along axis 21 between first and second positions.

More particularly, as discussed above, the engagement between first engagement arm 72, first intermediate member 74 and second intermediate member 76, and second engagement arm 94, third intermediate member 96 and fourth intermediate member 98 transfers rotational movement of shafts 84, 108 to engagement members 32, 52 positioned at proximal ends 26, 46 of first and second retractor portions 22, 42, respectively. As illustrated in FIG. 3, where the relative first and second positions of first and second retractor portions 22, 42 during rotation by actuating members 82, 106 is shown in phantom, the oscillation motion provided by actuating members 82, 106 of first and second retractor portions 22, 42 between the first and second positions may be relatively small. In one or more forms, it is contemplated that controller 128 may generally be used to control the amount or magnitude shafts 84, 108 are actuated to rotate first and second retractor portions 22, 42 and/or the frequency at which shafts 84, 108 are rotated during operation of the actuating members 82, 106 to move first and second retractor portions 22, 42 between the first and second positions. For example, in one particular form, it is contemplated that the oscillating motion could generally provide a vibratory or pulsating motion to first and second retractor portions 22, 42. In one form, it is contemplated that first and second retractor portions 22, 42 are oscillated at a frequency from about 10,000 Hz to about 0.001 Hz. In another form, it is also contemplated that first and second retractor portions 22, 42 may be oscillated at a frequency from about 1,000 Hz to about 0.01 Hz. Still, in yet another form, it is contemplated that first and second retractor portions 22, 42 may be oscillated at a frequency from about 10 Hz to about 0.1 Hz. Additionally, in one form, it is contemplated that the oscillation magnitude of first and second retractor portions 22, 42 is from about 0.01 mm to about 10 mm. Still, in another form, it is contemplated that the oscillation magnitude of first and second retractor portions 22, 42 is from about 0.1 mm to about 5 mm. However, it should be appreciated that alternative oscillation values for first and second retractor portions 22, 42 provided by actuating members 82, 106 are contemplated.

It should be appreciated that interface 134 and controller 128 may facilitate actuation of actuating members 82, 106 either alone or in combination with one another. In one particular form, upon responding to an actuation command received at controller 128, it is contemplated that one or both of actuating members 82, 106 will continually oscillate first and second retractor portions 22, 42 between the first and second positions until a command for halting actuation is received. In addition, it is also contemplated that controller 128 can be programmed to provide oscillation of first and second retractor portions 22, 42 in accordance with a predefined pattern, such as a sine wave, square-shaped wave, or triangular-shaped wave, just to provide a few possibilities. In another form however, controller 128 can be programmed to provide random oscillation of first and second retractor portions 22, 42. Still, it is also contemplated that controller 128 can be programmed with a variety of different oscillation patterns or profiles such that a user of system 10 can individually select an oscillation pattern suitable for a particular surgical application. It should be appreciated however that alternative arrangements for controlling performance of actuating members 82, 106 with controller 128 are contemplated.

In addition, in one or more forms, it is contemplated that system 10 can include one or more sensors configured to give feedback to controller 128. For example, the sensors may provide controller 128 with the distance by which first and second retractor portions 22, 42 have been separated, or may indicate the amount of pressure being applied to adjacent skin and tissue by first and second retractor portions 22, 42, just to provide a few possibilities. In these forms, dependent on the information received from the sensors, controller 128 may be programmed to automatically change an operating parameter of actuating members 82, 106 such that a closed loop control system is provided. Controller 128 may also be configured to record and store data pertaining to a surgical procedure performed with system 10. In one form, controller 128 may also be configured to provide an output to a user regarding the status of system 10. For example, a user could be provided with status updates throughout a surgical procedure, including the length of the procedure, the type of oscillation being providing or the amount of pressure being applied to adjacent skin and tissue, just to provide a few possibilities. Among other alternatives, it is contemplated that the output from controller 128 to a user could be in the form of an auditory signal and/or a visual signal.

Controller 128 operates in accordance with operating logic to actuate actuating members 82, 106 in accordance with an actuation command. Controller 128 is comprised of one or more components that may be configured as a single unit, or distributed among two or more units. Such components may be of a solid state, electromagnetic, optical, and/or different variety as would occur to those skilled in the art. Controller 128 may include analog circuitry, digital circuitry, and/or a hybrid combination of both of these types. In one form, controller 128 is of the programmable variety that executes algorithms and processes data in accordance with its operating logic being defined by programming instructions (such as software or firmware). Alternatively or additionally, the operating logic for controller 128 is at least partially defined by hardwired logic or other hardware. As illustrated in FIGS. 1 and 3, controller 128 includes power supply 136 which may supply power to controller 128 from an external source, such as an electrical socket. In another non-illustrated form, a power supply is located within internal controller 128 and may be provided for example, in the form of one or more electrochemical cells or battery of such cells. It should be appreciated that controller 128 may be modified for use with a DC power source or an AC power source and that the modification of components may be dependent upon the availability of one or more forms of the power source. Additional variations to controller 128 will become apparent with respect to various configurations of actuating members 82, 106.

In one particular embodiment where actuating members 82, 106 are in the form of electric motors, controller 128 controls the supply of electricity to actuating members 82, 106 in response to actuation commands. In another embodiment where actuating members 82, 106 are in the form of pneumatic motors, controller 128 controls a flow of compressed air between controller 128 and actuating members 82, 106 through pathways 130, 132. Controller 128 can be coupled with a source of compressed air or can include a compressor for generating compressed air. In response to an actuation command provided by a user at interface 134, controller 128 may actuate one or more valves to regulate the flow of compressed gas to one or both of actuating members 82, 106 and thereby start or stop rotation of shafts 84, 108. It is contemplated that the valve(s) may be positioned at controller 128 or at actuating members 82, 106. When the valves are positioned at controller 128, pathways 130, 132 are in the form of hollow tubing. In one variant of this form, it is contemplated that the tubing of pathways 130, 132 may be coaxial to provide compressed air to actuating members 82, 106 and also return air from actuating members 82, 106. Alternatively, one or more additional pathways may be provided between controller 128 and actuating members 82, 106 to facilitate the supply and return of compressed air. In another form where the valves are positioned at actuating members 82, 106, pathways 130, 132 may provide a control signal to the valves in addition to providing and returning compressed air. As an example, the valves may include an electro-mechanical configuration structured to operate in response to an electrical signal. Upon receiving an actuation command, controller 128 sends an electrical signal to the valves to actuate actuating members 82, 106 in accordance with the actuation commands.

In another embodiment where actuating members 82, 106 are in the form of hydraulic motors, controller 128 may be configured to regulate the flow of a hydraulic fluid to actuating members 82, 106. Examples of hydraulic fluids include water, water-based mixtures, oils, mineral oil, synthetic compounds and/or mixtures thereof, just to name a few possibilities. In this form, controller 128 may be coupled with a source of hydraulic fluid and include a combination of one or more pumps and valves to regulate the flow of hydraulic fluid between controller 128 and actuating members 82, 106 in response to a user actuation command provided at interface 134. It is contemplated that pathways 130, 132 may be provided as coaxial tubing to facilitate both the supply and return of hydraulic fluid to actuating members 82, 106.

One particular application for retractor system 10 is in spinal surgery. It is contemplated that, after insertion of first and second retractor portions 22, 42, they are separated predominantly in one direction to retract muscle and tissue along axis 21. For example, first and second retractor portions 22, 42 of retractor 20 can be primarily or predominantly separable in the direction of the spinal column axis. The muscle tissue adjacent the spine has a fiber orientation that extends generally in the direction of the spinal column axis. The separation of first and second retractor portions 22, 42 of retractor 20 can also separate the muscle tissue along the fibers, thus the amount of separation and the resultant tearing and trauma to the muscle tissue can be minimized. It is also contemplated in other techniques employing retractor 20 that working channel 50 can be enlarged primarily in a direction other than along the spinal column axis or in areas other than the spine.

In one example, a method for positioning first and second retractor portions 22, 42 through skin and tissue includes making an incision through the skin adjacent the location of a surgical site. For example, in spinal surgery, the incision can be made at a vertebral level at a location that provides access to the disc space between adjacent vertebrae or to one or more vertebra through a desired approach. Prior to insertion of first and second retractor portions 22, 42, the skin and tissue can be sequentially dilated via a dilation instrument set (not illustrated) which can include guidewires and/or one or more tissue dilators of increasing size. The tissue dilators are inserted one over another to form a pathway through the skin and tissue to the surgical site in the patient. In such procedures, first and second retractor portions 22, 42 are positioned over the last inserted dilator to form the pathway in the skin and tissue. Working channel 50 through first and second retractor portions 22, 42 provides access to a surgical site at the distal ends of first and second retractor portions 22, 42 when the guidewires and dilators, if used, are removed therefrom.

For the entire surgery or for certain procedures during the surgery, it may be desired by the surgeon to increase the size of working channel 50 to facilitate access to the surgical site. First and second retractor portions 22, 42 of retractor 20 can be separated from their insertion configuration by separation instrument 60 to a separated configuration in which working channel 50 is enlarged and exposed to skin and tissue along axis 21 while first and second retractor portions 22, 42 hold tissue out of the operative field. As first and second retractor portions 22, 42 are separated from one another, or after first and second retractor portions 22, 42 have been separated and are positioned in the separated configuration, one or both of first and second retractor portions 22, 42 can be rotated about axes 71, 91 and locked in a rotated position by locking assemblies 122, 124 as illustrated in FIG. 3. Once first and second retractor portions 22, 42 have been separated and rotated to a desired position, one or both of actuating members 82, 106 can be actuated to facilitate a rotational, oscillating motion of first and second retractor portions 22, 42 along axis 21 and relative to the adjacent skin and tissue. In one form, the rotational, oscillating motion of first and second retractor portions 22, 42 may only be performed during one or more portions of the surgery, although it is also contemplated that the rotational, oscillating motion of first and second retractor portions 22, 42 may be continually performed throughout the entire surgery or as long as first and second retractor portions 22, 42 of retractor 20 are separated and retracting the adjacent skin and tissue. Still, in other forms, it is contemplated that one or both of actuating members 82, 106 can be actuated to facilitate a rotational, oscillating motion of first and second retractor portions 22, 42 along axis 21 and relative to the adjacent skin and tissue as first and second retractor portions 22, 42 are separated along axis 21.

Figure 4:
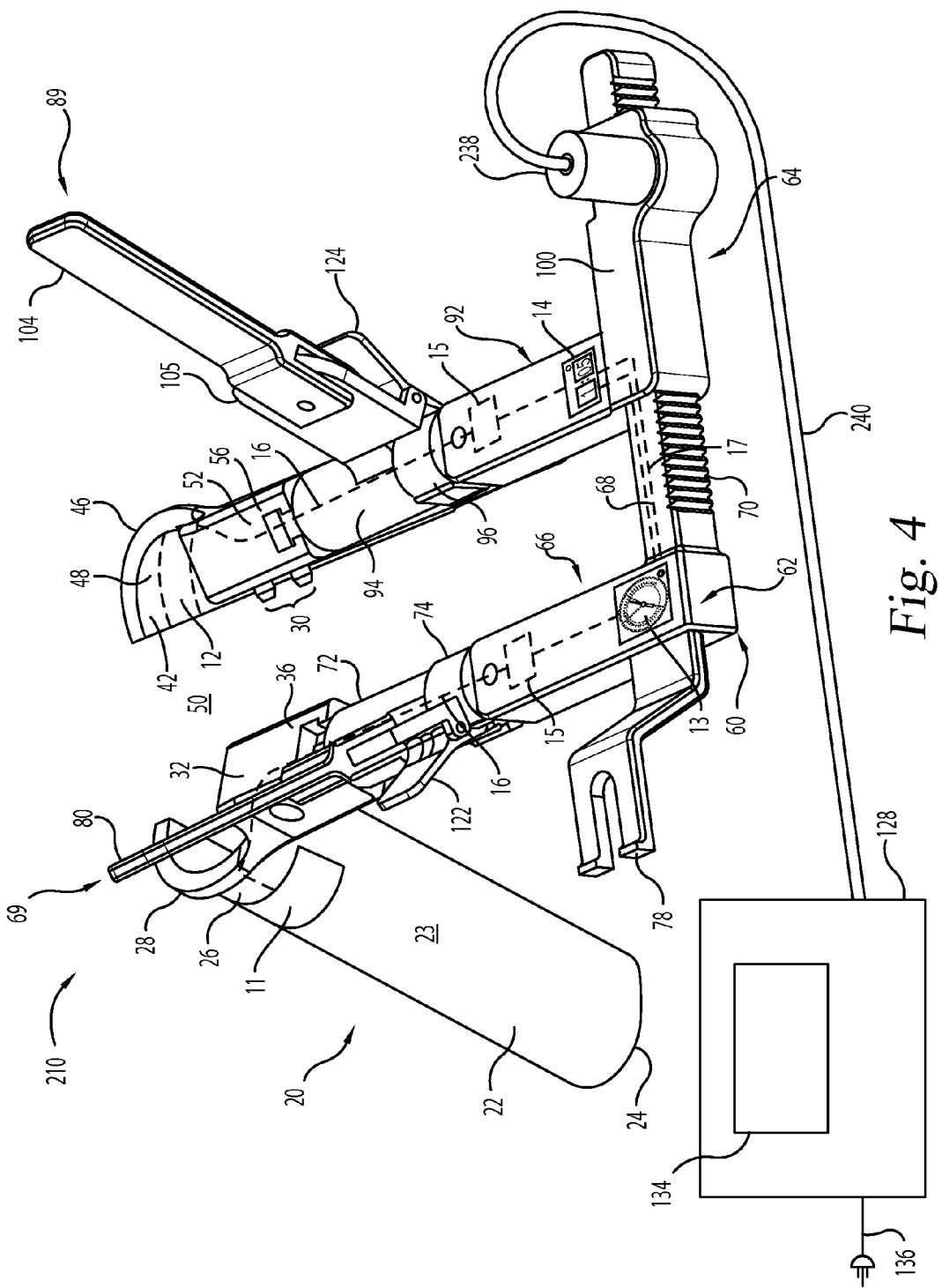
FIG. 4 is a perspective view of an alternative embodiment retractor system.

An alternative embodiment retractor system 210 is illustrated in a perspective view in FIG. 4, where like numerals refer to like features of retractor system 10 previously described. In contrast to retractor system 10, retractor 20 of system 210 does not include actuating members 82, 106 and first connection assembly 62 does not include intermediate member 76, while second connection assembly 64 does not include intermediate member 98. Similarly, as illustrated in FIG. 4, intermediate member 74 is fixedly coupled to first extension arm 66 and intermediate member 96 is fixedly coupled to second extension arm 92. Additionally, adjustment mechanism 102 and locking mechanism 120 have been replaced by an actuating member 238. Actuating member 238 includes a gear wheel that engages with ratchet teeth 70 along coupling arm 68 to effect movement of coupling arm 68 in housing 100 and provide a desired separation distance between first and second retractor portions 22, 42. In one form, actuating member 238 may be provided as an electric, pneumatic or hydraulic motor that rotates the gear wheel, although other types of actuating members including mechanical vibrators and ultrasonic motion generators are also contemplated, as well as alternative arrangements for moving second connection member 64 and second retractor portion 42.

Once a desired separation distance between first and second retractor portions 22, 42 has been obtained, actuating member 238 maintains separation of first and second retractor portions 22, 42 during surgery, and is also operable to laterally translate second connection member 64 along coupling arm 68 in an oscillating motion during the surgery between first and second positions, thereby providing similar movement to second retractor portion 42. In one or more forms, it is contemplated that controller 128 may generally be used to control the amount actuating member 238 is actuated to laterally displace second connection member 64 and second retractor portion 42 along coupling arm 68 and/or the frequency at which actuating member 238 is actuated to move second connection member 64 and second retractor portion 42 between the first and second positions. Moreover, similar to the arrangement discussed above with respect to system 10, it is contemplated that the distance which second connection member 64 may be moved back and forth between the first and second positions may be relatively small. For example, in one particular form, it is contemplated that the oscillating motion could generally provide a vibratory or pulsating motion along second connection member 64 and second retractor portion 42. Moreover, the magnitude and frequency of oscillation provided by actuating member 238 may generally correspond to the values discussed above with respect to system 10. However, it should be appreciated that alternative oscillation values of second connection member 64 and second retractor portion 42 provided by actuating member 238 between the first and second positions are contemplated. Still, in other forms, it is contemplated that actuating member 238 can be actuated to facilitate a translational, oscillating motion of first and second retractor portions 22, 42 along axis 21 and relative to the adjacent skin and tissue as first and second retractor portions 22, 42 are separated along axis 21.

Actuating member 238 is connected by pathway 240 to controller 128 such that controller 128 and actuating member 238 are in communication with one another. While controller 128 is positioned remotely to actuating member 238 in the illustrated form, it should be appreciated that controller 128 could also be integrated into actuating member 238. Moreover, in one or more alternative forms, it should be appreciated that system 210 may be provided with a wireless communication interface between controller 128 and actuating member 238. In response to an actuation command provided at controller 128, actuating member 238 laterally displaces second connection member 64 and second retractor portion 42 in an oscillating fashion as discussed above. In one particular form, upon responding to an actuation command received at controller 128, it is contemplated that actuating member 238 will continually laterally displace and oscillate second connection member 64 and second retractor portion 42 between the first and second positions along coupling arm 68 until a command for halting actuation is received. In addition, it is also contemplated that controller 128 can be programmed to provide oscillation of second connection member 64 and second retractor portion 42 in accordance with a predefined pattern as discussed above with respect to system 10. Alternatively, controller 128 can be programmed to provide random oscillation of second connection member 64 and second retractor portion 42. Still, it is also contemplated that controller 128 can be programmed with a variety of different oscillation patterns or profiles such that a user of system 210 can individually select an oscillation pattern suitable for a particular surgical application. It should be appreciated however that alternative arrangements for controlling performance of actuating member 238 with controller 128 are contemplated. Moreover, it should also be appreciated that controller 128 in system 210 can generally correspond to and be configured the same as or substantially similar to the configuration of controller 128 as described above with respect to system 10.

Similar to retractor system 10, retractor system 210 may also be used in spinal surgery. In one form, it is contemplated that, after insertion of first and second retractor portions 22, 42 through an incision in skin and/or tissue, an actuation command may be provided at controller 150 to separate first and second retractor portions 22, 42 along axis 21 with actuating member 238 until a desired spacing of first and second retractor portions 22, 42 is obtained. As first and second retractor portions 22, 42 are separated from one another, or after first and second retractor portions 22, 42 have been separated and are positioned in the separated configuration, one or both of first and second retractor portions 22, 42 can be rotated and locked in a rotated position by locking assemblies 122, 124. Once the desired configuration of working channel 50 has been obtained, an additional actuation command can be provided at controller 128 to maintain the working channel in the desired configuration with the actuating member 238 and/or to laterally displace second connection member 64 and second retractor portion 42 with the actuating member 238 in an oscillating fashion along coupling arm 68 and axis 21 and relative to first connection arm 62 and first retractor portion 22. In one form, the laterally displacing, oscillating motion of second connection member 64 and second retractor portion 42 may only be performed during one or more portions of the surgery, although it is also contemplated that the laterally displacing, oscillating motion of second connection member 64 and second retractor portion 42 may be continually performed throughout the entire surgery or as long as first and second retractor portions 22, 42 of retractor 20 are separated and retracting the adjacent skin and tissue.

Figure 5:
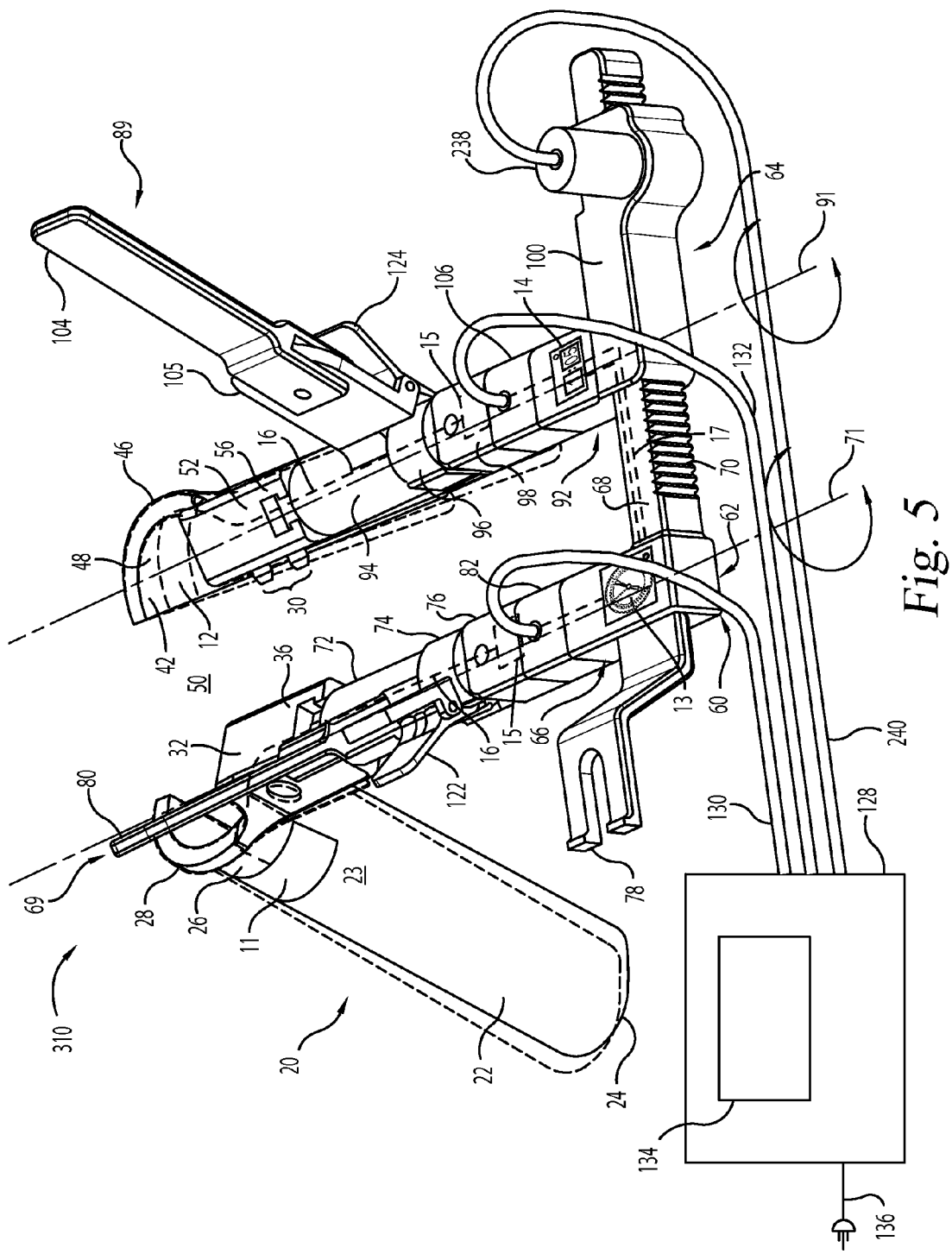
FIG. 5 is a perspective view of another alternative embodiment retractor system.

Another alternative embodiment retractor system 310 is illustrated in perspective view in FIG. 5, where like numerals refer to like features of retractor systems 10, 210 previously described. Retractor system 310 is substantially similar to retractor system 10 except that adjustment mechanism 102 and locking mechanism 120 have been replaced by actuating member 238, similar to the arrangement of retractor system 210. Likewise, retractor system 310 is operable to provide a rotational, oscillating motion of first and second retractor portions 22, 42 along axis 21 and relative to the adjacent skin and tissue as described above with respect to system 10, as well as a laterally displacing, oscillating motion of second connection member 64 and second retractor portion 42 as described above with respect to system 210. In one alternative form, it is contemplated that the laterally displacing, oscillating motion provided by actuating member 238 could be provided in an embodiment where only one of first and second connection members 62, 64 includes an actuating member that provides the rotational, oscillating motion of its respective retractor portion.

Similar to retractor systems 10, 210, retractor system 310 may also be used in spinal surgery. In one form, it is contemplated that, after insertion of first and second retractor portions 22, 42 through an incision in skin and/or tissue, an actuation command may be provided at controller 128 to separate first and second retractor portions 22, 42 with actuating member 238 along axis 21 until a desired spacing of first and second retractor portions 22, 42 is obtained. As first and second retractor portions 22, 42 are separated from one another, or after first and second retractor portions 22, 42 have been separated and are positioned in the separated configuration, one or both of first and second retractor portions 22, 42 can be rotated about axes 71, 91 and locked in a rotated position by locking assemblies 122, 124.

Once the desired configuration of working channel 50 has been obtained, an additional actuation command can be provided at controller 128 to maintain the working channel in the desired configuration with the actuating member 238, to provide the rotational, oscillating motion of one or both of first retractor portion 22 and second retractor portion 42 with actuating members 82 and 106, respectively, and/or to laterally displace second connection member 64 and second portion 42 with actuating member 238 in an oscillating fashion along coupling arm 68 and axis 21 and relative to first connection arm 62 and first retractor portion 22. In one form, the rotational, oscillating motion of one or both of first retractor portion 22 and second retractor portion 42 and/or the laterally displacing, oscillating motion of second connection member 64 and second retractor portion 42 may only be performed during one or more portions of the surgery, although it is also contemplated that the rotational, oscillating motion of one or both of first retractor portion 22 and second retractor portion 42 and the laterally displacing, oscillating motion of second connection member 64 and second retractor portion 42 may be continually performed throughout the entire surgery or as long as first and second retractor portions 22, 42 of retractor 20 are separated and retracting the adjacent skin and tissue, although alternative oscillation patterns are contemplated as discussed above with respect to systems 10 and 210. While not previously mentioned, it should also be appreciated that controller 128 in system 310 can generally correspond to and be configured the same as or substantially similar to the configuration of controller 128 as described above with respect to systems 10 and 210.

Figure 6:
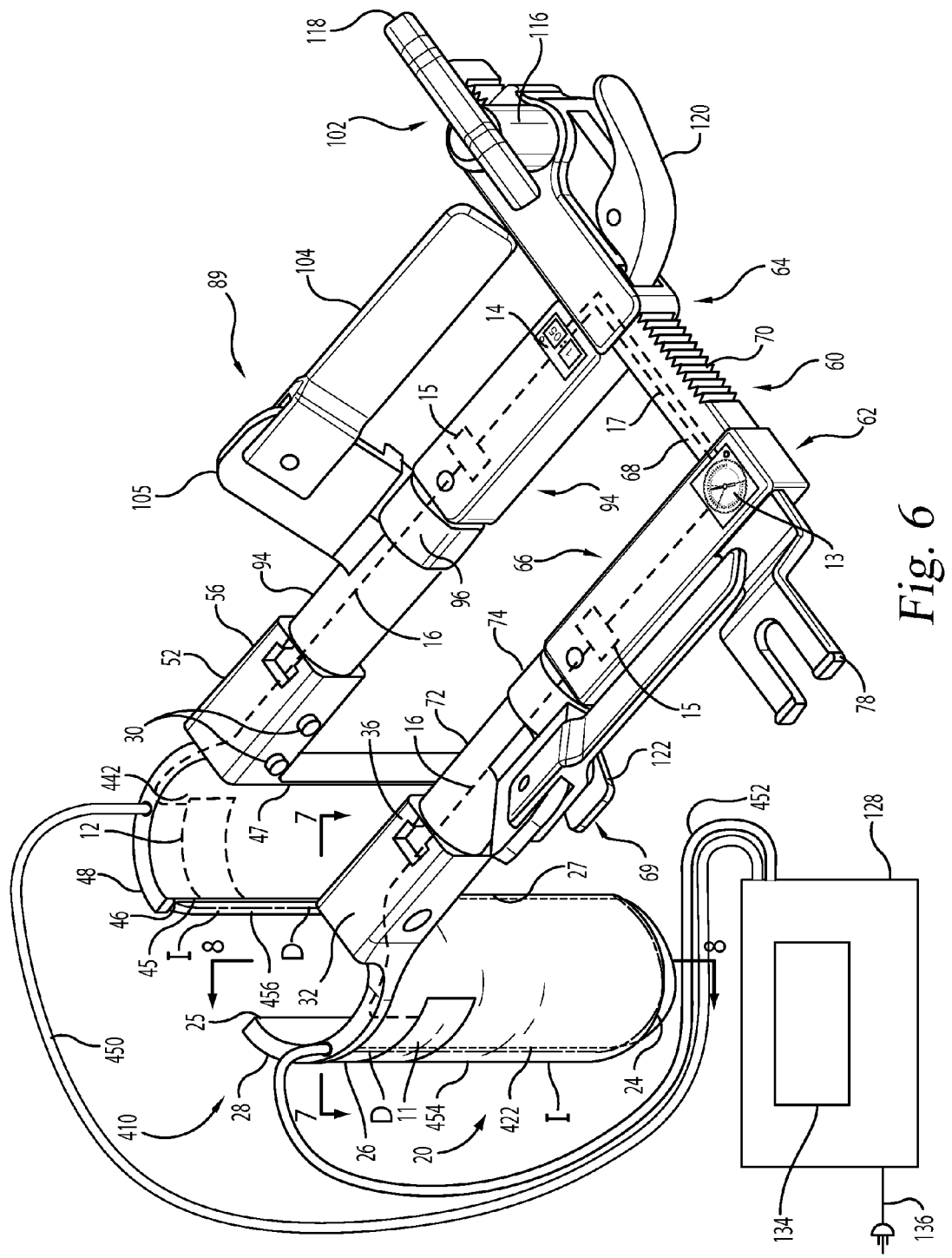
FIG. 6 is a perspective view of yet another alternative embodiment retractor system.

Another alternative embodiment retractor system 410 is illustrated in perspective view in FIG. 6, where like numerals refer to like features of retractor system 10 previously described. In contrast to retractor system 10, retractor 20 of system 410 does not include actuating members 82, 106 and first connection assembly 62 does not include intermediate member 76, while second connection assembly 64 does not include intermediate member 98. Similarly, as illustrated in FIG. 6, intermediate member 74 is fixedly coupled to first extension arm 66 and intermediate member 96 is fixedly coupled to second extension arm 92. Additionally, retractor 20 includes first and second retractor portions 422, 442 that are configured alternatively to first and second retractor portions 22, 42 of retractor system 10. For example, each of first and second retractor portions 422, 442 are generally expandable in a lateral between their interior surfaces which line working channel 50 and their exterior surfaces which are positioned against adjacent skin and tissue.

Figure 7A:
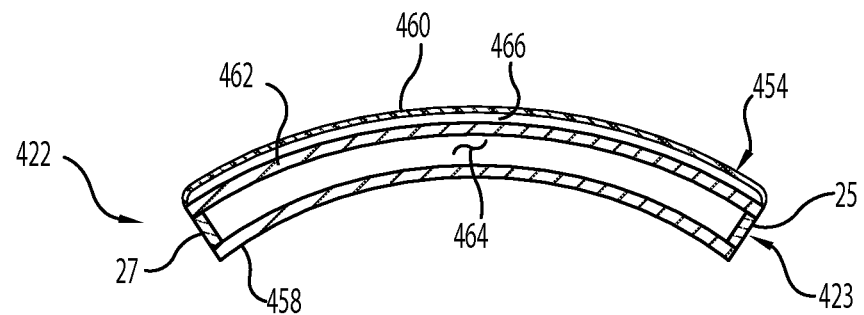
FIGS. 7A and 7B are section views of one of the retractor portions of the system of FIG. 6 in a non-expanded configuration and an expanded configuration, respectively.
Figure 7B:
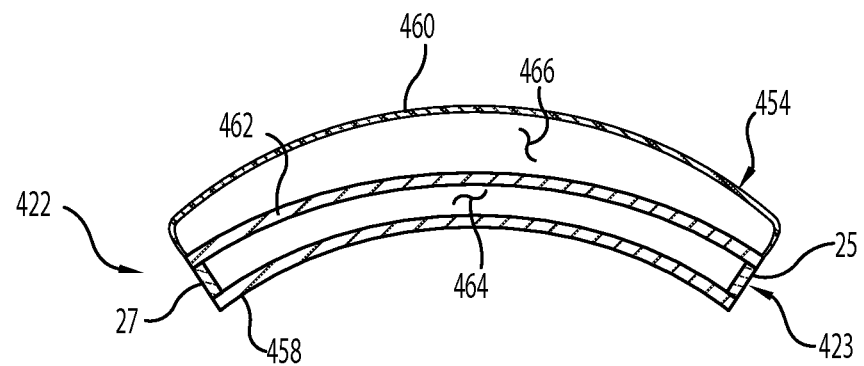
Figure 8:
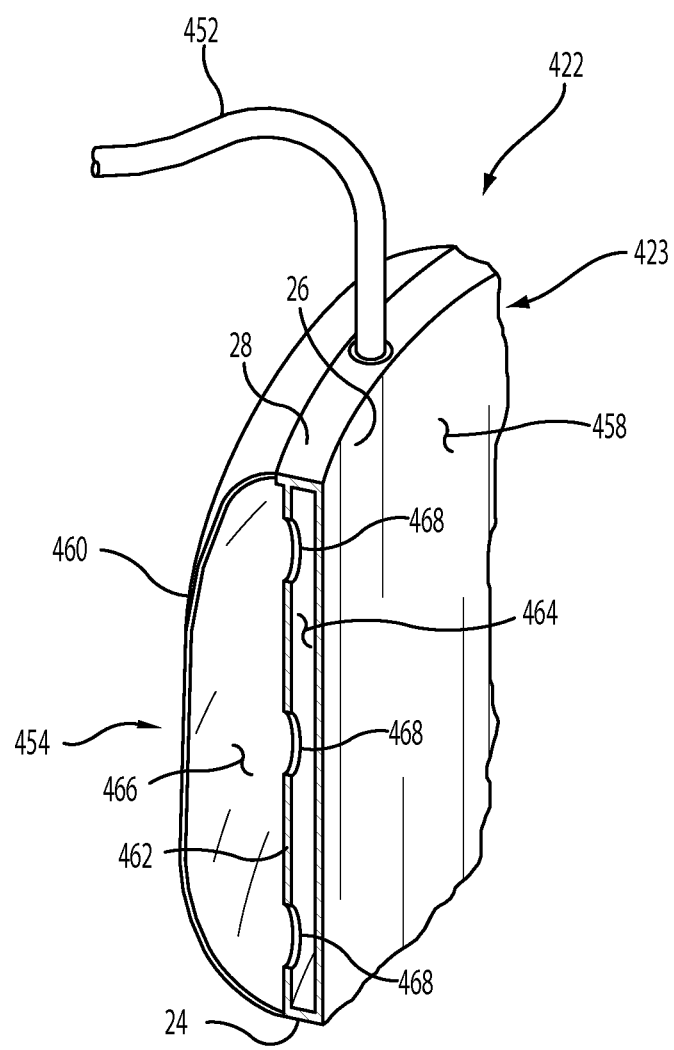
FIG. 8 is an alternative, partially cut-away section view of the retractor portion illustrated in FIGS. 7A and 7B in an expanded configuration.

More particularly, in the illustrated form, first retractor portion 422 is provided with an inflatable balloon 454 along its exterior surface and second retractor portion 442 is provided with an inflatable balloon 456 along its exterior surface. As shown in FIG. 6, each of balloons 454, 456 are positionable between an inflated position I and a deflated position D. It should be appreciated however that balloons 454, 456 are also positionable at an infinite number of positions between inflated position I and deflated position D. With further regard to first retractor portion 422, FIGS. 7A and 7B provide cross sectional views thereof illustrating its inflated and deflated positions. First retractor portion 422 includes a body 423 that extends between distal end 24 and proximal end 26. Body 423 includes an interior surface 458 that extends along and lines working channel 50. An exterior surface 460 is positioned opposite interior surface 458 and generally comes in contact with skin and tissue adjacent body 423 when first retractor portion 422 is inserted into an incision. Balloon 454 generally defines exterior surface 460 and is engaged to body 423 along longitudinal edges 25, 27. Additionally, as illustrated in FIG. 8, balloon 454 is also engaged to body 423 adjacent to distal end 24 and proximal end 26. In this configuration, an internal chamber 466 is positioned between balloon 454 and an intermediate wall 462 that is positioned between interior surface 458 and exterior surface 460.

An internal chamber 464 is also positioned between intermediate wall 462 and interior surface 458. A pathway 452 which may be used to supply an inflating medium, such as compressed air or gas or some other type of fluid, is engaged with collar 28 such that internal chamber 464 is in fluid communication with pathway 452. Intermediate wall 462 is also provided with a plurality of passages 468 that facilitate flow of the inflating medium between internal chamber 464 and internal chamber 466. As internal chamber 466 is progressively filled with the inflating medium, balloon 454 gradually expands to the configuration illustrated in FIGS. 7B and 8. Moreover, as the inflating medium is progressively removed from internal chamber 466, balloon 454 gradually returns to the configuration illustrated in FIG. 7A. In this arrangement, the distance between interior surface 458 and exterior surface 460 can be continually changed across an infinite number of positions between the inflated and deflated positions. Still, other forms for first retraction portion 422 are contemplated. For example, in one non-illustrated form, body 423 may be provided without intermediate wall 462 such that only a single internal chamber between exterior surface 460 and interior surface 458 is provided. In this configuration, the single internal chamber is in direct communication with the inflating medium as it is delivered through pathway 452. Similarly, pathway 452 is also in direct communication with the inflating medium in the single internal chamber as the inflating medium is removed therefrom.

It should be appreciated that one or both of interior surface 458 or intermediate wall 462, if present, can be provided with sufficient rigidity between their distal and proximal ends to separate and maintain separation of adjacent tissue when first and second retractor portions 422, 442 are initially inserted and also when the adjacent tissue is retracted by moving first retractor portion 422 and second retractor portion 442 away from one another. For example, interior surface 458 or intermediate wall 462 can include a thickness which provides sufficient rigidity to resist bending or bowing under the forces exerted on it by the retracted tissue and/or muscle, as well as any additional pressure added by inflation of balloon 454. In addition, while the foregoing features have been described with respect to first retractor portion 422, it should be appreciated that second retractor portion 442 may be provided with similar features and operate in a similar manner.

First and second retractor portions 422, 442 communicate with controller 128 via pathways 450, 452. In the illustrated form, pathways 450, 452 engage with first and second retractor portions 422, 442 at collars 28, 48, respectively, although other configurations for engagement of pathways 450, 452 are contemplated. For example, in one non-illustrated form, pathways 450, 452 may be coupled with engagement members 32, 52 which include an internal conduit for supplying the inflating medium from pathways 450, 452 to balloons 454, 456. In another form, it is contemplated that retractor portion 20 could be provided with internal conduits extending through first and second connection members 62, 64 into communication with an internal chamber of balloons 454, 456 such that pathways 450, 452 may be engaged with first and second connection members 62, 64 near coupling arm 68.

Controller 128, which can be configured as described above with respect to system 10, may generally be utilized to control inflation and deflation of balloon members 454, 456 to their inflated and deflated positions, or to any position therebetween. In one particular form, it is contemplated that controller 128 may generally be used to control the amount of inflating media which is present in balloons 454, 456 at any given time and/or the frequency at which balloons 454, 456 are inflated or deflated to change the distance between the interior and exterior surfaces of first and second retractor portions 422, 442, thereby providing an oscillating-type of motion to first and second retractor portions 422, 442. In one particular form, upon responding to an actuation command, it is contemplated that controller 128 will begin a timed inflating and deflating sequence of balloons 454, 456 and continually perform this sequence until a command for halting the same is received. However, similar to the oscillation provided by system 10 as discussed above, it should be appreciated that alternative arrangements for controlling inflation and deflation of balloons 454, 456 with controller 128 are contemplated.

In one embodiment where the inflating medium is compressed air or gas, controller 128 controls a flow of compressed air or gas between controller 128 and balloons 454, 456 through pathways 450, 452 and removal of compressed air or gas from balloons 454, 456 through pathways 450, 452. Controller 128 can be coupled with a source of compressed air or gas or can include a compressor for generating compressed air, and can also be provided with or connected to a vacuum source operable to remove compressed air or gas from balloons 454, 456 as appropriate. In response to an actuation command provided by a user at interface 134, controller 128 may actuate one or more valves to regulate the flow of compressed air or gas to or from one or both of balloons 454, 456 and thereby start or stop inflation or deflation of balloons 454, 456. In one form, it is contemplated that the valve(s) may be positioned at controller 128. When the valves are positioned at controller 128, pathways 450, 452 are in the form of hollow tubing. In one variant of this form, it is contemplated that the tubing of pathways 450, 452 may be coaxial to provide compressed air or gas to balloons 450, 452 and also return air or gas from balloons 454, 456. Alternatively, one or more additional pathways may be provided between controller 128 and balloons 454, 456 to facilitate the supply and return of compressed air or gas. It should further be appreciated that in alternative embodiments where the inflating medium is a different fluid such as water, a water-based mixture, oils, mineral oil, synthetic compounds and/or mixtures thereof, controller 128 may be similarly configured to the arrangement discussed above to control inflation and deflation of balloons 454, 456 with the respective inflating medium.

Similar to retractor system 10, retractor system 410 may also be used in spinal surgery. In one form, it is contemplated that, after insertion of first and second retractor portions 422, 442 through an incision in skin and/or tissue, separation instrument 60 can be used to separate first and second retractor portions 422, 442 until a desired separation of first and second retractor portions 422, 442 is obtained. As first and second portions retractor portions 422, 442 are separated from one another, or after first and second retractor portions 422, 442 have been separated and are positioned in the separated configuration, one or both of first and second retractor portions 422, 442 can be rotated and locked in a rotated position by locking assemblies 122, 124. Once the desired configuration of working channel 50 has been obtained, an actuation command can be provided at controller 128 to begin an inflating and deflating sequence of balloons 454, 456 to provide a continuous or periodic change in the configuration of first and second retractor portions 422, 442 relative to the adjacent skin and tissue. For example, the distance between the interior and exterior surfaces of the first and second retractor portions 422, 442 may be continuously or periodically changed. Stated alternatively, the outer profiles of the retractor portions 422, 442 can generally be oscillated between first and second positions as balloons 454, 456 are inflated and deflated. In one form, the inflating and deflating sequence may generally provide a vibratory or pulsating motion to balloons 454, 456. In addition, the inflating and deflating sequence may only be performed during one or more portions of the surgery, although it is also contemplated that the inflating and deflating sequence of one or both of balloons 454, 456 may be continually performed throughout the entire surgery or as long as first and second retractor portions 422, 442 of retractor 20 are separated and retracting the adjacent skin and tissue. However, it should be appreciated that the inflation and deflation sequence of balloons 454, 456 may be performed in a manner similar to the oscillation described above with respect to system 10. For example, it is contemplated that balloons 454, 456 can be inflated and deflated randomly or in accordance with one or more patterns programmed in controller 128. As another example, it is contemplated that controller 128 can control the magnitude to which, and/or the frequency at which, balloons 454, 456 are inflated and deflated.

In one embodiment, a retractor system for percutaneous surgery in a patient includes a first retractor portion including a proximal end and a distal end positionable in an incision. A second retractor portion includes a proximal end and a distal end positionable in the incision opposite the first retractor portion. The first and second retractor portions define an axis extending therebetween. The system also includes at least one actuating member operable to provide a first oscillating motion to at least one of the first and second retractor portions. A controller is provided in communication with the actuating member and the actuation member is responsive to the controller to oscillate the at least one of the first and second retractor portions between a first position and a second position.

In another embodiment, a method for retracting tissue for percutaneous access to a surgical site in a patient is provided. The method includes providing a retractor including a first retractor portion including a proximal end and a distal end positionable in an incision and a second retractor portion including a proximal end and a distal end positionable in the incision opposite the first retractor portion. The first and second retractor portions define an axis extending therebetween. The method also includes positioning the first and second retractor portions relative to each other along the axis in an open configuration to provide a working channel therebetween, and oscillating at least one of the first and second retractor portions between a first position and a second position when the first and second retractor portions are in the open configuration.

In still another embodiment, a retractor blade includes a body that includes a first surface and an oppositely positioned second surface. The first and second surfaces extend between a proximal end and a distal end of the body. The body is expandable between the oppositely positioned surfaces from a first configuration to a second configuration. In the first configuration, a first distance separates the oppositely positioned surfaces which is dissimilar to a second distance that separates the oppositely positioned surfaces in the second configuration.

The retractors and retractor systems described herein also have application with other types of instruments and implants, and may be used in other portions of the body besides the spine. The retractors and retractor systems described herein may also be used in surgical procedures involving animals, or in demonstrations for training, education, marketing, sales and/or advertising purposes. In addition, the retractors and retractor systems may be also used on or in connection with a non-living subject such as a cadaver, training aid or model, or in connection with testing of surgical systems, surgical procedures, orthopedic devices and/or apparatus.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. A retractor system for percutaneous surgery in a patient, comprising:
    a first connection assembly comprising a first lever assembly and a first retractor portion including a proximal end and a distal end positionable in an incision, said first retractor portion including a concave inner surface and a convex outer surface opposite said inner surface;
    a second connection assembly comprising a second lever assembly and a second retractor portion including a proximal end and a distal end positionable in the incision opposite the first retractor portion, said second retractor portion including a concave inner surface facing said inner surface of said first retractor portion and a convex outer surface opposite said inner surface of said second retractor portion, said first and second retractor portions defining a first axis extending therebetween, said first and second lever assemblies being operable to rotate said first and second retractor portions about their proximal ends to move their distal ends away from each other;
    a controller in communication with said first and second retractor portions, wherein said first and/or second retractor portions is responsive to said controller to cause movement of said first and said second retractor portions between a first position in which the retractor portions are parallel and a second position in which the retractor portions are transverse independent of the lever assemblies;
    at least one pressure sensor configured to sense pressure applied to tissue that engages said first and second retractor portions and being configured to generate a sensor signal representative of said pressure;
    a timing circuit in communication with said at least one pressure sensor; and
    a separation instrument defining a separation axis and engaging first and second connection members that extend from said first and second connection assemblies, said separation instrument being operable to move said retractor portions toward one another and away from one another along the first axis without said separation instrument rotating about said separation axis.

2. The retractor system of claim 1 wherein said timing circuit is configured to start timing upon the generation of said sensor signal representative of said pressure from said at least one pressure sensor and stop timing upon the cessation of said sensor signal representative of said pressure from said at least one pressure sensor.

3. The retractor system of claim 2 further comprising at least one display for displaying said signal representative of said pressure and/or for displaying time elapsed between said start and said stop of said timing circuit, and/or displaying an integrated pressure-time value.

4. The retractor system of claim 2 wherein said timing circuit is in communication with one display for displaying the time elapsed between said start and said stop of said timing circuit and/or display for an integrated pressure-time value, and said at least one pressure sensor is in communication with a second display for displaying the pressure signal and/or display for an integrated pressure-time value.

5. The retractor system of claim 4 wherein said display for displaying said signal representative of said pressure comprises a face-plate having a plurality of colors inscribed thereon wherein each color represents a range of different pressures; and an indicator disposed upon said face-plate, said display in communication with a transponder of said pressure sensor for indicating at least one of said colors.

6. The retractor system of claim 4 wherein said integrated pressure-time value display for displaying the integrated pressure-time comprises a face-plate having a plurality of colors inscribed thereon wherein each color represents a range of different integrated pressure-time values; and an indicator disposed upon said face-plate, said display in communication with said at least one pressure sensor and said timing circuit for indicating at least one of said colors.

7. The retractor system of claim 1 further comprising an actuating member operably connected to said first and said second retractor portions in a configuration to cause movement of at least one of said first and second retractor portions.

8. The retractor system of claim 7 further comprising a transponder in communication with said pressure sensor, said transponder responsive to said pressure sensor for converting said sensor signal to a pressure signal representative of said pressure.

9. The system of claim 7, wherein said separation instrument is offset to one side of said first axis and comprises ratchet teeth that engage a gear wheel of said separation instrument, the gear wheel being spaced apart from the controller.

10. The system of claim 7, wherein said actuating member is positioned on said first connection member between said separation instrument and said first retractor portion such that said actuating member is coaxial with said first connection member, and a first oscillating motion includes rotation of said proximal end of said first retractor portion about a first rotation axis extending transverse to said proximal end between said first and second positions when said first and second retractor portions are in a second configuration.

11. The system of claim 10, further comprising a second actuating member positioned on said second connection member between said separation instrument and said second retractor portion such that said separation instrument extends through a passage in said second connection member that is coaxial with said separation axis, said second actuating member being operable to provide a second oscillating motion to said second retractor portion, said second oscillating motion including rotation of said proximal end of said second retractor portion about a second rotation axis extending transverse to said proximal end between a third position and a fourth position when said first and second retractor portions are in said second configuration.

12. A method for retracting tissue for percutaneous access to a surgical site in a patient, comprising:
providing the retractor of claim 5;
positioning said first and second retractor portions relative to each other along said first axis in an open configuration to provide a working channel there between;
inserting said first and second retractor portions into an incision and moving at least one of said first and second retractor portions between the first position and the second position so as to apply pressure to tissue in contact with said first and second retractor portions of said retractor;
measuring and/or displaying a values of said pressure applied to said tissue in contact with said first and second retractor portions of said retractor tissue using said pressure sensor and/or a display;
measuring and/or displaying the amount of time said pressure is applied to said tissue in contact with said first and second retractor portions of said retractor using the timing circuit and/or said display; and
determining if said pressure or said time said pressure is applied to said or said integrated pressure-time value is above a pre-determined level and adjusting said first and said second retractor portions between said first position and said second position if said pressure applied by said retractor or said time or said integrated pressure-time value in which said pressure is applied is/are above a pre-determined value.

13. The retractor system of claim 1 further comprising an actuating member operable to provide a first oscillating motion to at least one of said first and second retractor portions; said controller being in communication with said actuating member, wherein said actuating member is responsive to said controller to oscillate said at least one of said first and second retractor portions between said first position and said second position, wherein said controller includes a user interface for receiving actuation commands from the user and wherein said actuating member is operable to respond to the actuation commands to oscillate said at least one of said first and second retractor portions.

14. The system of claim 13, wherein said first oscillating motion includes lateral movement of said first retractor portion between said first and second positions.

15. The system of claim 14, wherein said first oscillating motion includes rotation of said proximal end of said first retractor portion about a first rotational axis such that said distal end of said first retractor portion moves back and forth relative to said second retractor portion.

16. The system of claim 15, further comprising a second actuating member operable to provide a second oscillating motion to said second retractor portion, said second oscillating motion including rotation of said proximal end of said second retractor portion between a third position and a fourth position about a second rotation axis extending transverse to said proximal end.

17. The system of claim 13, further comprising a second actuating member operable to provide a second oscillating motion to said first retractor portion, said second oscillating motion including rotation of said proximal end of said first retractor portion between a third position and a fourth position about a first rotation axis extending transverse to said proximal end.

18. The retractor system of claim 1, wherein said first and second connection assemblies each comprise an engagement member coupled to a respective retractor portion, and said first and second lever assemblies each comprise a lever arm pivotably mounted to a mounting member, the mounting member being engaged with a respective engagement member.

19. The retractor system of claim 1, further comprising an actuating member positioned between said first retractor portion and said separation instrument so as to prevent said actuating member from rotating about an axis extending parallel to said first axis.

20. The retractor system of claim 1, further comprising an actuating member defining an actuating axis, said actuating member being positioned between said first retractor portion and said separation instrument to limit movement of said actuating member relative to said first connection member to movement along said actuating axis and to prevent said actuating member from moving relative to said separation instrument in a direction that is transverse to said actuating axis.

21. A retractor system for percutaneous surgery in a patient, comprising:
- a first connection assembly comprising a first retractor portion including a proximal end and a distal end positionable in an incision;
- a second connection assembly comprising a second retractor portion including a proximal end and a distal end positionable in the incision opposite the first retractor portion, said first and second retractor portions defining a first axis extending therebetween;
- a controller in communication with said retractor portions, wherein said retractor portions are responsive to said controller to cause movement of said retractor portions between a first position in which said retractor portions are separated by a first distance and a second position in which said retractor portions are separated by a second distance that is greater than the first distance;
- at least one pressure sensor configured to sense pressure applied to tissue that engages said retractor portions and being configured to generate a sensor signal representative of said pressure;
- a separation instrument defining a separation axis and being coupled between first and second connection members extending from said proximal ends, said separation instrument being operable to move said retractor portions toward one another and away from one another along the first axis without rotating the separation instrument about said separation axis;
- a timing circuit in communication with said at least one pressure sensor; and
- an actuating member configured to cause movement of at least one of said first and second retractor portions, said actuating member being positioned between said first retractor portion and said separation instrument so as to prevent said actuating member from rotating about an axis extending parallel to said first axis, said controller being in communication with said actuating member, wherein said actuating member is responsive to said controller to oscillate said first and second retractor portions between said first position and said second position, wherein said controller includes a user interface for receiving actuation commands from the user and wherein said actuating member is operable to respond to the actuation commands to oscillate said at least one of said first and second retractor portions.

22. A retractor system for percutaneous surgery in a patient, comprising:
- a first connection assembly comprising a first lever assembly and a first retractor portion including a proximal end and a distal end positionable in an incision, said first retractor portion including a concave inner surface and a convex outer surface opposite said inner surface;
- a second connection assembly comprising a second lever assembly and a second retractor portion including a proximal end and a distal end positionable in the incision opposite the first retractor portion, said second retractor portion including a concave inner surface facing said inner surface of said first retractor portion and a convex outer surface opposite said inner surface of said second retractor portion, said first and second retractor portions defining a first axis extending therebetween, said first and second lever assemblies being operable to rotate said first and second retractor portions about their proximal ends to move their distal ends away from each other;
- a controller in communication with said first and second retractor portions, wherein said first and/or second retractor portions is responsive to said controller to rotate said first and said second retractor portions relative to one another;
- at least one pressure sensor configured to sense pressure applied to tissue that engages said first and second retractor portions and being configured to generate a sensor signal representative of said pressure;
- a timing circuit in communication with said pressure sensor, said timing circuit being configured to begin timing upon the generation of said sensor signal representative of said pressure from said at least one pressure sensor and stop timing upon the cessation of said sensor signal representative of said pressure from said at least one pressure sensor;
- a separation instrument defining a separation axis and engaging first and second connection members that extend from said first and second connection assemblies, said separation instrument being operable to move said retractor portions toward one another and away along the first axis from one another without said separation instrument rotating about said separation axis; and
- an actuating member operable to provide a first oscillating motion to at least one of said first and second retractor portions, said controller being in communication with said actuating member, wherein said actuating member is responsive to said controller to oscillate said first and second retractor portions between a first position and a second position, wherein said controller includes a user interface for receiving actuation commands from the user and wherein said actuating member is operable to respond to the actuation commands to oscillate said at least one of said first and second retractor portions.

* * * * *